US011851510B2

(12) United States Patent
Carter et al.

(10) Patent No.: US 11,851,510 B2
(45) Date of Patent: Dec. 26, 2023

(54) LOW VISCOSITY PHOTO-CURABLE RESINS FOR THE DIRECT FABRICATION OF ORTHODONTIC APPLIANCES

(71) Applicant: Align Technology, Inc., San Jose, CA (US)

(72) Inventors: Blaine Carter, San Jose, CA (US); Jennifer Chavez, Fremont, CA (US); Lance Robert Pickens, Campbell, CA (US); Michael Christopher Cole, Longmont, CO (US); Peter Dorfinger, Los Altos Hills, CA (US); Yan Chen, Cupertino, CA (US)

(73) Assignee: Align Technology, Inc., San Jose, CA (US)

( * ) Notice: Subject to any disclaimer, the term of this patent is extended or adjusted under 35 U.S.C. 154(b) by 0 days.

(21) Appl. No.: 17/190,308

(22) Filed: Mar. 2, 2021

(65) Prior Publication Data
US 2021/0277152 A1 Sep. 9, 2021

Related U.S. Application Data

(60) Provisional application No. 62/984,075, filed on Mar. 2, 2020.

(51) Int. Cl.
*C08F 2/50* (2006.01)
*A61L 27/16* (2006.01)
(Continued)

(52) U.S. Cl.
CPC ............... *C08F 2/50* (2013.01); *A61L 27/14* (2013.01); *A61L 27/16* (2013.01); *C08F 20/34* (2013.01); *C08K 5/14* (2013.01)

(58) Field of Classification Search
CPC ...... C08F 2/50; C08F 20/34; C08F 222/1065; C08F 220/1818; C08K 5/14; A61L 27/14; A61L 27/16; A61L 27/00
See application file for complete search history.

(56) References Cited

U.S. PATENT DOCUMENTS

| 5,820,368 A | 10/1998 | Wolk |
| 5,975,893 A | 11/1999 | Chishti et al. |

(Continued)

FOREIGN PATENT DOCUMENTS

| WO | WO-2015075094 A1 | 5/2015 |
| WO | WO-2016078838 A1 | 5/2016 |
| WO | WO-2018032022 A1 | 2/2018 |

OTHER PUBLICATIONS

Wikipedia contributors. (Jan. 10, 2023). Viscosity. In Wikipedia, The Free Encyclopedia. Retrieved 20:21, Jan. 14, 2023, from https://en.wikipedia.org/w/index.php?title=Viscosity&oldid=1132845934 (Year: 2023).*

(Continued)

*Primary Examiner* — Sanza L. McClendon
(74) *Attorney, Agent, or Firm* — Seed IP Law Group LLP

(57) ABSTRACT

This disclosure provides low-viscosity resins for producing polymers with properties suitable for use in various mechanical appliances, such as orthodontic appliances (e.g., aligners). The low-viscosity resins may be photo-curable and can be used with direct fabrication methods and equipment. In various embodiments, the polymeric materials produced from the low-viscosity resins described herein have high toughness while remaining resistant to stress relaxation. Low-viscosity, photo-curable resins described herein have reduced hydrogen bonding in comparison to traditional materials (e.g., materials having high urethane content) used in orthodontic appliances.

28 Claims, 6 Drawing Sheets

(51) Int. Cl.
*C08F 20/34* (2006.01)
*C08K 5/14* (2006.01)
*A61L 27/14* (2006.01)

(56) References Cited

U.S. PATENT DOCUMENTS

| | | |
|---|---|---|
| 6,183,248 B1 | 2/2001 | Chishti et al. |
| 6,309,215 B1 | 10/2001 | Phan et al. |
| 6,386,864 B1 | 5/2002 | Kuo |
| 6,450,807 B1 | 9/2002 | Chishti et al. |
| 6,454,565 B2 | 9/2002 | Phan et al. |
| 6,471,511 B1 | 10/2002 | Chishti et al. |
| 6,524,101 B1 | 2/2003 | Phan et al. |
| 6,572,372 B1 | 6/2003 | Phan et al. |
| 6,607,382 B1 | 8/2003 | Kuo et al. |
| 6,705,863 B2 | 3/2004 | Phan et al. |
| 6,749,414 B1 | 6/2004 | Hanson et al. |
| 6,783,604 B2 | 8/2004 | Tricca |
| 6,790,035 B2 | 9/2004 | Tricca et al. |
| 6,814,574 B2 | 11/2004 | Abolfathi et al. |
| 6,830,450 B2 | 12/2004 | Knopp et al. |
| 6,947,038 B1 | 9/2005 | Anh et al. |
| 7,074,039 B2 | 7/2006 | Kopelman et al. |
| 7,104,792 B2 | 9/2006 | Taub et al. |
| 7,121,825 B2 | 10/2006 | Chishti et al. |
| 7,160,107 B2 | 1/2007 | Kopelman et al. |
| 7,192,273 B2 | 3/2007 | McSurdy, Jr. |
| 7,347,688 B2 | 3/2008 | Kopelman et al. |
| 7,354,270 B2 | 4/2008 | Abolfathi et al. |
| 7,448,514 B2 | 11/2008 | Wen |
| 7,481,121 B1 | 1/2009 | Cao |
| 7,543,511 B2 | 6/2009 | Kimura et al. |
| 7,547,735 B1 * | 6/2009 | Konarski ............ C08L 19/006 522/18 |
| 7,553,157 B2 | 6/2009 | Abolfathi et al. |
| 7,600,999 B2 | 10/2009 | Knopp |
| 7,658,610 B2 | 2/2010 | Knopp |
| 7,766,658 B2 | 8/2010 | Tricca et al. |
| 7,771,195 B2 | 8/2010 | Knopp et al. |
| 7,854,609 B2 | 12/2010 | Chen et al. |
| 7,871,269 B2 | 1/2011 | Wu et al. |
| 7,878,801 B2 | 2/2011 | Abolfathi et al. |
| 7,878,805 B2 | 2/2011 | Moss et al. |
| 7,883,334 B2 | 2/2011 | Li et al. |
| 7,892,474 B2 | 2/2011 | Shkolnik et al. |
| 7,914,283 B2 | 3/2011 | Kuo |
| 7,947,508 B2 | 5/2011 | Tricca et al. |
| 8,152,518 B2 | 4/2012 | Kuo |
| 8,172,569 B2 | 5/2012 | Matty et al. |
| 8,235,715 B2 | 8/2012 | Kuo |
| 8,292,617 B2 | 10/2012 | Brandt et al. |
| 8,337,199 B2 | 12/2012 | Wen |
| 8,401,686 B2 | 3/2013 | Moss et al. |
| 8,517,726 B2 | 8/2013 | Kakavand et al. |
| 8,562,337 B2 | 10/2013 | Kuo et al. |
| 8,641,414 B2 | 2/2014 | Borovinskih et al. |
| 8,684,729 B2 | 4/2014 | Wen |
| 8,708,697 B2 | 4/2014 | Li et al. |
| 8,758,009 B2 | 6/2014 | Chen et al. |
| 8,771,149 B2 | 7/2014 | Rahman et al. |
| 8,899,976 B2 | 12/2014 | Chen et al. |
| 8,899,977 B2 | 12/2014 | Cao et al. |
| 8,936,463 B2 | 1/2015 | Mason et al. |
| 8,936,464 B2 | 1/2015 | Kopelman |
| 9,022,781 B2 | 5/2015 | Kuo et al. |
| 9,119,691 B2 | 9/2015 | Namiranian et al. |
| 9,161,823 B2 | 10/2015 | Morton et al. |
| 9,241,774 B2 | 1/2016 | Li et al. |
| 9,326,831 B2 | 5/2016 | Cheang |
| 9,388,267 B2 * | 7/2016 | Kurata .................... C08L 51/06 |
| 9,433,476 B2 | 9/2016 | Khardekar et al. |
| 9,610,141 B2 | 4/2017 | Kopelman et al. |
| 9,655,691 B2 | 5/2017 | Li et al. |
| 9,675,427 B2 | 6/2017 | Kopelman |
| 9,700,385 B2 | 7/2017 | Webber |
| 9,744,001 B2 | 8/2017 | Choi et al. |
| 9,844,424 B2 | 12/2017 | Wu et al. |
| 10,045,835 B2 | 8/2018 | Boronkay et al. |
| 10,111,730 B2 | 10/2018 | Webber et al. |
| 10,150,244 B2 | 12/2018 | Sato et al. |
| 10,201,409 B2 | 2/2019 | Mason et al. |
| 10,213,277 B2 | 2/2019 | Webber et al. |
| 10,299,894 B2 | 5/2019 | Tanugula et al. |
| 10,363,116 B2 | 7/2019 | Boronkay |
| 10,383,705 B2 | 8/2019 | Shanjani et al. |
| D865,180 S | 10/2019 | Bauer et al. |
| 10,449,016 B2 | 10/2019 | Kimura et al. |
| 10,463,452 B2 | 11/2019 | Matov et al. |
| 10,470,847 B2 | 11/2019 | Shanjani et al. |
| 10,492,888 B2 | 12/2019 | Chen et al. |
| 10,517,701 B2 | 12/2019 | Boronkay |
| 10,537,406 B2 | 1/2020 | Wu et al. |
| 10,537,463 B2 | 1/2020 | Kopelman |
| 10,548,700 B2 | 2/2020 | Fernie |
| 10,555,792 B2 | 2/2020 | Kopelman et al. |
| 10,588,776 B2 | 3/2020 | Cam et al. |
| 10,613,515 B2 | 4/2020 | Cramer et al. |
| 10,639,134 B2 | 5/2020 | Shanjani et al. |
| 10,743,964 B2 | 8/2020 | Wu et al. |
| 10,758,323 B2 | 9/2020 | Kopelman |
| 10,781,274 B2 | 9/2020 | Liska et al. |
| 10,813,720 B2 | 10/2020 | Grove et al. |
| 10,874,483 B2 | 12/2020 | Boronkay |
| 10,881,487 B2 | 1/2021 | Cam et al. |
| 10,912,629 B2 | 2/2021 | Tanugula et al. |
| 10,959,810 B2 | 3/2021 | Li et al. |
| 10,993,783 B2 | 5/2021 | Wu et al. |
| 2002/0192617 A1 | 12/2002 | Phan et al. |
| 2004/0166462 A1 | 8/2004 | Phan et al. |
| 2004/0166463 A1 | 8/2004 | Wen et al. |
| 2005/0014105 A1 | 1/2005 | Abolfathi et al. |
| 2005/0186524 A1 | 8/2005 | Abolfathi et al. |
| 2005/0244768 A1 | 11/2005 | Taub et al. |
| 2006/0019218 A1 | 1/2006 | Kuo |
| 2006/0078841 A1 | 4/2006 | Desimone et al. |
| 2006/0115782 A1 | 6/2006 | Li et al. |
| 2006/0115785 A1 | 6/2006 | Li et al. |
| 2006/0199142 A1 | 9/2006 | Liu et al. |
| 2006/0234179 A1 | 10/2006 | Wen et al. |
| 2008/0118882 A1 | 5/2008 | Su |
| 2008/0160473 A1 | 7/2008 | Li et al. |
| 2008/0268400 A1 | 10/2008 | Moss et al. |
| 2008/0286716 A1 | 11/2008 | Sherwood |
| 2008/0286717 A1 | 11/2008 | Sherwood |
| 2009/0280450 A1 | 11/2009 | Kuo |
| 2010/0055635 A1 | 3/2010 | Kakavand |
| 2010/0129763 A1 | 5/2010 | Kuo |
| 2011/0269092 A1 | 11/2011 | Kuo et al. |
| 2014/0061974 A1 | 3/2014 | Tyler |
| 2014/0067334 A1 | 3/2014 | Kuo |
| 2014/0265034 A1 | 9/2014 | Dudley |
| 2015/0097315 A1 | 4/2015 | DeSimone et al. |
| 2015/0097316 A1 | 4/2015 | DeSimone et al. |
| 2015/0102532 A1 | 4/2015 | DeSimone et al. |
| 2015/0265376 A1 | 9/2015 | Kopelman |
| 2015/0366637 A1 | 12/2015 | Kopelman et al. |
| 2015/0366638 A1 | 12/2015 | Kopelman et al. |
| 2016/0193014 A1 | 7/2016 | Morton et al. |
| 2016/0242870 A1 | 8/2016 | Matov et al. |
| 2016/0242871 A1 | 8/2016 | Morton et al. |
| 2017/0007359 A1 | 1/2017 | Kopelman et al. |
| 2017/0007360 A1 | 1/2017 | Kopelman et al. |
| 2017/0007361 A1 | 1/2017 | Boronkay et al. |
| 2017/0007365 A1 | 1/2017 | Kopelman et al. |
| 2017/0007366 A1 | 1/2017 | Kopelman et al. |
| 2017/0007386 A1 | 1/2017 | Mason et al. |
| 2017/0135792 A1 | 5/2017 | Webber |
| 2017/0135793 A1 | 5/2017 | Webber et al. |
| 2017/0165032 A1 | 6/2017 | Webber et al. |
| 2017/0319296 A1 | 11/2017 | Webber et al. |
| 2018/0153648 A1 | 6/2018 | Shanjani et al. |
| 2018/0153733 A1 | 6/2018 | Kuo |
| 2018/0168776 A1 | 6/2018 | Webber |
| 2018/0353264 A1 | 12/2018 | Riley et al. |

(56) References Cited

U.S. PATENT DOCUMENTS

| | | |
|---|---|---|
| 2018/0360567 A1 | 12/2018 | Xue et al. |
| 2018/0368944 A1 | 12/2018 | Sato et al. |
| 2019/0000592 A1 | 1/2019 | Cam et al. |
| 2019/0000593 A1 | 1/2019 | Cam et al. |
| 2019/0021817 A1 | 1/2019 | Sato et al. |
| 2019/0029775 A1 | 1/2019 | Morton et al. |
| 2019/0046297 A1 | 2/2019 | Kopelman et al. |
| 2019/0069975 A1 | 3/2019 | Cam et al. |
| 2019/0099129 A1 | 4/2019 | Kopelman et al. |
| 2019/0125494 A1 | 5/2019 | Li et al. |
| 2019/0125497 A1 | 5/2019 | Derakhshan et al. |
| 2019/0152152 A1 | 5/2019 | O'Leary et al. |
| 2019/0175304 A1 | 6/2019 | Morton et al. |
| 2019/0231477 A1 | 8/2019 | Shanjani et al. |
| 2019/0262101 A1 | 8/2019 | Shanjani et al. |
| 2019/0298494 A1 | 10/2019 | Webber et al. |
| 2019/0314119 A1 | 10/2019 | Kopelman et al. |
| 2019/0338067 A1 | 11/2019 | Liska et al. |
| 2019/0343606 A1 | 11/2019 | Wu et al. |
| 2020/0000553 A1 | 1/2020 | Makarenkova et al. |
| 2020/0086553 A1 | 3/2020 | Mojdeh et al. |
| 2020/0100864 A1 | 4/2020 | Wang et al. |
| 2020/0100865 A1 | 4/2020 | Wang et al. |
| 2020/0100866 A1 | 4/2020 | Medvinskaya et al. |
| 2020/0100871 A1 | 4/2020 | Wang et al. |
| 2020/0155276 A1 | 5/2020 | Cam et al. |
| 2020/0188062 A1 | 6/2020 | Kopelman et al. |
| 2020/0214598 A1 | 7/2020 | Li et al. |
| 2020/0214801 A1 | 7/2020 | Wang et al. |
| 2020/0390523 A1 | 12/2020 | Sato et al. |
| 2021/0078357 A1 | 3/2021 | Venkatasanthanam et al. |

OTHER PUBLICATIONS

Tumbleston et al., "Continuous Liquid Interface Production of 3D Objects. Science", (Mar. 2015), vol. 347.6228: pp. 1349-1352.

DYMAX Corporation., "BOMAR BRC-4421 Difunctional Aliphatic Hydrophobic Urethane Acrylate", Product Datasheet, Feb. 20, 2019, 2 pages, XP002803291, Retrieved from the Internet [URL: https://dymax-oc.com/images/pdf/pds/brc-4421.pdf].

\* cited by examiner

LOW VISCOSITY PHOTO-CURABLE RESINS FOR THE DIRECT FABRICATION OF ORTHODONTIC APPLIANCES

CROSS-REFERENCE

This application claims the benefit of U.S. Provisional Patent Application No. 62/984,075 filed on Mar. 2, 2020, the entire contents of which are incorporated herein by reference.

BACKGROUND OF THE INVENTION

Low viscosity resins are common and facilitate the use of 3D printing of polymers using conventional 3D printers. However, low viscosity resins traditionally do not produce polymers that are hard, tough, and resistant to stress relaxation. When producing polymeric orthodontic appliances such as aligners, it is desirable that the polymer of the aligners have material properties of hardness, toughness, and resistance to stress relaxation. As such, traditional low viscosity resins are not compatible with the production of orthodontic appliances.

SUMMARY OF THE INVENTION

Provided herein are photo-curable resins having low viscosity. Such resins have applications for use, including in direct fabrication of appliances (e.g., orthodontic appliances). Also provided herein are objects manufactured using the photo-curable low-viscosity resins, materials made from the photo-curable low-viscosity resins, and methods of using the photo-curable low-viscosity resins.

In various aspects, the present disclosure provides a photo-curable resin comprising an oligomer having a number-average molecular weight of greater than 3,000 Da; and an initiator, wherein the photo-curable resin comprises less than 20 wt % hydrogen bonding units and has a viscosity less than or equal to 15,000 cP at 25° C.

In various aspects, the present disclosure provides a photo-curable resin comprising an oligomer having a number-average molecular weight of greater than 3,000 Da; and a photoinitiator, wherein the photo-curable resin comprises less than 10 wt % hydrogen bonding units.

In some aspects, the photo-curable resin comprises less than 15 wt %, less than 10 wt %, less than 9 wt %, less than 8 wt %, less than 7 wt %, less than 6 wt %, less than 5 wt %, less than 4 wt %, less than 3 wt %, less than 2 wt %, or less than 1 wt % hydrogen bonding units. In some aspects, a polymeric material formed from the photo-curable resin comprises a water uptake of less than 25 wt %, less than 20 wt %, less than 15 wt %, less than 10 wt %, less than 5 wt %, less than 4 wt %, less than 3 wt %, less than 2 wt %, less than 1 wt %, less than 0.5 wt %, less than 0.25 wt %, or less than 0.1 wt %. In some aspects, the number-average molecular weight of the oligomer is from 9 kDa to 20 kDa.

In some aspects, the oligomer comprises a plurality of monomers, and the average chain length of the oligomer is from 20 to 200 monomers. In some aspects, the photo-curable resin has a viscosity from 30 cP to 50,000 cP at a printing temperature. In some aspects, the printing temperature is from 20° C. to 150° C. In some aspects, the initiator comprises a photoinitiator. In some aspects, the initiator comprises a thermal initiator. In some aspects, the thermal initiator comprises an organic peroxide. In some aspects, the resin further comprises a reactive diluent. In some aspects, the resin further comprises a crosslinking modifier, a light blocker, a solvent, a glass transition temperature modifier, or a combination thereof. In some aspects, the photo-curable resin comprises less than 90% of the solvent by weight.

In some aspects, the oligomer comprises an aliphatic urethane (meth)acrylate. In some aspects, the oligomer comprises two or more functional groups. In some aspects, the oligomer is difunctional. In some aspects, the oligomer is monofunctional. In some aspects, the photo-curable resin comprises a plurality of oligomers, and wherein the plurality of oligomers comprise a monofunctional oligomer, a difunctional oligomer, a multifunctional oligomer, or a combination thereof. In some aspects, a polymer formed from the oligomer is hydrophobic. In some aspects, a polymeric material formed from the photo-curable resin is hydrophobic.

In some aspects, the photo-curable resin comprises 0.5-99.5 wt % of the oligomer, 1-99 wt % of the oligomer, 10-95 wt % of the oligomer, 20-90 wt % of the oligomer, 25-60 wt % of the oligomer, or 35-50 wt % of the oligomer. In some aspects, the photo-curable resin comprises 25-60 wt % of the oligomer. In some aspects, the photo-curable resin comprises 99.5 wt % or less of the oligomer. In some aspects, the photo-curable resin comprises 10-75 wt % of the reactive diluent, 15-60 wt % of the reactive diluent, 20-50 wt % of the reactive diluent, 25-45 wt % of the reactive diluent, or 30-40 wt % of the reactive diluent. In some aspects, the photo-curable resin comprises 20-50 wt % of the reactive diluent. In some aspects, the crosslinking modifier is a reactive diluent.

In some aspects, the photo-curable resin comprises 0-25 wt % of the crosslinking modifier, the crosslinking modifier having a number-average molecular weight equal to or less than 3,000 Da, equal to or less than 2,500 Da, equal to or less than 2,000 Da, equal to or less than 1,500 Da, equal to or less than 1,250 Da, equal to or less than 1,000 Da, equal to or less than 800 Da, equal to or less than 600 Da, or equal to or less than 400 Da. In some aspects, the photo-curable resin comprises 0-25 wt % of the crosslinking modifier, the crosslinking modifier having a number-average molecular weight equal to or less than 1,500 Da.

In some aspects, the photo-curable resin comprises 0.01-10 wt %, 0.02-5 wt %, 0.05-4 wt %, 0.1-3 wt %, 0.1-2 wt %, or 0.1-1 wt % of the photoinitiator. In some aspects, the photo-curable resin comprises 0.1-2 wt % of the photoinitiator. In some aspects, the photo-curable resin comprises from 0 to 10 wt %, from 0 to 9 wt %, from 0 to 8 wt %, from 0 to 7 wt %, from 0 to 6 wt %, from 0 to 5 wt %, from 0 to 4 wt %, from 0 to 3 wt %, from 0 to 2 wt %, from 0 to 1 wt %, or from 0 to 0.5 wt % of the light blocker. In some aspects, the photo-curable resin comprises from 0 to 0.5 wt % of the light blocker.

In some aspects, the photo-curable resin comprises from 0 to 10 wt %, from 0 to 9 wt %, from 0 to 8 wt %, from 0 to 7 wt %, from 0 to 6 wt %, from 0 to 5 wt %, from 0 to 4 wt %, from 0 to 3 wt %, from 0 to 2 wt %, from 0 to 1 wt %, or from 0 to 0.5 wt % of the thermal initiator. In some aspects, the photo-curable resin comprises from 0 to 0.5 wt % of the thermal initiator.

In some aspects, the reactive diluent comprises an acrylate, a methacrylate, or a combination thereof. In some aspects, the reactive diluent comprises a (meth)acrylate, a di(meth)acrylate, a di(meth)acrylate of polyglycols, a hydrobenzoic acid ester (meth)acrylate, a cycloalkyl-2-, 3-, or 4-((meth)acryloxy)benzoate, isobornyl (meth)acrylate, isobornyl (meth)acrylate, trimethylolpropane tri(meth)acrylate, triethylene glycol di(meth)acrylate, TEGDMA, 1,12-dodecanediol di(meth)acrylate, D4MA, 3,3,5-trimethcyclohexyl 2-((meth)acryloxy) benzoate, HSMA, benzyl salicylate (meth)acrylate, BSMA, 3,3,5-Trimethylcyclohexyl (meth)acrylate, tripropylene glycol di(meth)acrylate, hexane-1,6-diol di(meth)acrylate, tricyclodecanedimethanol di(meth)acrylate, hydroxyethyl (meth)acrylate, benzyl (meth)acrylate, a (poly)vinyl monomer, a derivative thereof, or a combination thereof. In some aspects, the reactive diluent comprises an acrylate or methacrylate. In some aspects, the reactive diluent comprises a (poly)glycol di(meth)acrylate, a triethylene glycol di(meth)acrylate, a tetraethylene glycol di(meth)acrylate, bisphenol A di(meth)acrylate, a hydrogenated form of bisphenol A di(meth)acrylate, a methacrylate- or acrylate-terminated polyester oligomer, 4,4'-isopropylidenedicyclohexanol di(meth)acrylate, a salicylic ester (meth)acrylate, or cycloalkyl salicylate (meth) acrylate. In some aspects, the reactive diluent comprises a (poly)vinyl monomer. In some aspects, the reactive diluent comprises vinyl acetate, styrene, or divinylbenzene.

In some aspects, the crosslinking modifier comprises an acrylate-terminated polyester, a tricyclodecanediol diacrylate, a methacrylate-terminated polyester, a tricyclodecanediol di(meth)acrylate, a vinyl ester-terminated polyester, a tricyclodecanediol vinyl ester, or a combination thereof. In some aspects, the photoinitiator comprises diphenyl (2,4,6-trimethylbenzoyl)-phosphine oxide, ethyl (2,4,6-trimethylbenzoyl) phenyl phosphinate, or a combination thereof.

In some aspects, the photoinitiator comprises a radical photoinitiator, a cationic initiator, and/or a photobase generator. In some aspects, the photoinitiator is a Type I photoinitiator which undergoes a unimolecular bond cleavage to generate free radicals, or a Type II photoinitiator which undergoes a bimolecular reaction to generate free radicals. In some aspects, the Type I photoinitiator is a benzoin ether, a benzil ketal, an α-dialkoxy-acetophenone, an α-hydroxy-alkyl phenome, or an acyl-phosphine oxide. In some aspects, the Type II photoinitiator is a benzophenone/amine or a thioxanthone/amine. In some aspects, the cationic initiators is an aryldiazonium, a diaryliodonium, or a triarylsulfonium salt. In some aspects, the photoinitiator initiates photopolymerization with exposure to light energy from 800 nm to 250 nm, from 800 nm to 350 nm, from 800 nm to 450 nm, from 800 nm to 550 nm, from 800 nm to 650 nm, from 600 nm to 250 nm, from 600 nm to 350 nm, from 600 nm to 450 nm, or from 400 nm to 250 nm. In some aspects, the light blocker comprises 2-(2'-hydroxy-phenyl benzotriazole), 2,2'-dihydroxy-4-methoxybenzophenone, 9,10-diethoxyanthracene, a hydroxyphenyltriazine, an oxanilide, a benzophenone, or a combination thereof.

In some aspects, the thermal initiator comprises azobisisobutyronitrile, 2,2'-azodi(2-methylbutyronitrile), or a combination thereof.

In some aspects, the viscosity is: less than 1,000 cP at 110° C.; less than 1,000 cP at 90° C.; less than 500 cP at 70° C.; less than 200 cP at 90° C.; or less than 10,000 cP at 25° C. In some aspects, the viscosity is less than 50,000 cP, less than 40,000 cP, less than 30,000 cP, less than 25,000 cP, less than 20,000 cP, less than 15,000 cP, less than 10,000 cP, or less than 5,000 cP at a print temperature. In some aspects, the viscosity is less than 20,000 cP at a print temperature. In some aspects, the print temperature is from 10° C. to 200° C., from 15° C. to 175° C., from 20° C. to 150° C., from 25° C. to 125° C., or from 30° C. to 100° C. In some aspects, the print temperature is from 20° C. to 150° C.

In some aspects, the photo-curable resin is capable of being 3D printed.

In various aspects, the present disclosure provides a method of forming a polymeric material, the method comprising: providing the photo-curable resin disclosed herein; and curing the photo-curable resin, thereby forming the polymeric material. In some aspects, the polymeric material comprises less than or equal to 10 wt % hydrogen bonding units. In some aspects, the polymeric material is characterized by one or more of: a tensile modulus greater than or equal to 200 MPa; a flexural stress of greater than or equal to 1.5 MPa remaining after 24 hours in a wet environment at 37° C.; a hardness from 60 Shore A to 85 Shore D; and an elongation at break greater than or equal to 15%.

In some aspects, the polymeric material has greater than 60% conversion of double bonds to single bonds, as measured by FTIR. In some aspects, the polymeric material has less than 5 wt % extractable materials. In some aspects, the polymeric material is characterized by a water uptake of less than 25 wt %, less than 20 wt %, less than 15 wt %, less than 10 wt %, less than 5 wt %, less than 4 wt %, less than 3 wt %, less than 2 wt %, less than 1 wt %, less than 0.5 wt %, less than 0.25 wt %, or less than 0.1 wt %.

In some aspects, curing the photo-curable resin comprises exposing the photo-curable resin to a light source. In some aspects, the method further comprises heating the polymeric material to an elevated temperature. In some aspects, the elevated temperature is from 40° C. to 150° C. In some aspects, heating the polymeric material to the elevated temperature occurs after curing the photo-curable resin.

In some aspects, the method further comprises fabricating an object with the polymeric material. In some aspects, fabricating the object comprises additive manufacturing. In some aspects, fabricating the object with the polymeric material comprises printing with a 3D printer. In some aspects, fabricating the object with the polymeric material comprises digital light projection. In some aspects, fabricating the object with the polymeric material comprises high temperature lithography.

In some aspects, the object is an orthodontic appliance. In some aspects, the orthodontic appliance is an aligner, expander or spacer. In some aspects, the orthodontic appliance comprises a plurality of tooth receiving cavities configured to reposition teeth from a first configuration toward a second configuration. In some aspects, the orthodontic appliance is one of a plurality of orthodontic appliances configured to reposition the teeth from an initial configuration toward a target configuration. In some aspects, the orthodontic appliance is one of a plurality of orthodontic appliances configured to reposition the teeth from an initial configuration toward a target configuration according to a treatment plan.

In various aspects, the present disclosure provides a polymeric material produced by a method described herein. In some aspects, the polymeric material has less than 20 wt %, less than 15 wt %, less than 10 wt %, less than 9 wt %, less than 8 wt %, less than 7 wt %, less than 6 wt %, less than 5 wt %, less than 4 wt %, less than 3 wt %, less than 2 wt %, or less than 1 wt % hydrogen bonding units. In some aspects, the polymeric material comprises a water uptake of less than 25 wt %, less than 20 wt %, less than 15 wt %, less than 10 wt %, less than 5 wt %, less than 4 wt %, less than 3 wt %, less than 2 wt %, less than 1 wt %, less than 0.5 wt %, less than 0.25 wt %, or less than 0.1 wt %.

In various aspects, the present disclosure provides a polymeric material formed from the photo-curable resin described herein. In some aspects, the polymeric material has less than 20 wt %, less than 15 wt %, less than 10 wt %, less than 9 wt %, less than 8 wt %, less than 7 wt %, less than 6 wt %, less than 5 wt %, less than 4 wt %, less than 3 wt %, less than 2 wt %, or less than 1 wt % hydrogen bonding units. In some aspects, the polymeric material comprises a water uptake of less than 25 wt %, less than 20 wt %, less than 15 wt %, less than 10 wt %, less than 5 wt %, less than 4 wt %, less than 3 wt %, less than 2 wt %, less than 1 wt %, less than 0.5 wt %, less than 0.25 wt %, or less than 0.1 wt %.

In various aspects, the present disclosure provides a polymeric material comprising a polymer, the polymeric material having less than 10 wt % hydrogen bonding units, wherein the polymeric material is characterized by one or more of: a tensile modulus greater than or equal to 200 MPa after 24 hours in a wet environment at 37° C.; a flexural stress of greater than or equal to 1.5 MPa remaining after 24 hours in a wet environment at 37° C.; a hardness from 60 Shore A to 85 Shore D after 24 hours in a wet environment at 37° C.; and an elongation at break greater than or equal to 15% after 24 hours in a wet environment at 37° C.

In some aspects, the polymeric material is characterized by a water uptake of less than 25 wt %, less than 20 wt %, less than 15 wt %, less than 10 wt %, less than 5 wt %, less than 4 wt %, less than 3 wt %, less than 2 wt %, less than 1 wt %, less than 0.5 wt %, less than 0.25 wt %, or less than 0.1 wt %. In some aspects, the water uptake is measured after 24 hours in a wet environment at 37° C. In some aspects, the polymeric material has greater than 60% conversion of double bonds to single bonds, as measured by FTIR. In some aspects, the polymeric material has less than 5 wt % extractable materials. In some aspects, the polymeric material comprises less than 9 wt %, less than 8 wt %, less than 7 wt %, less than 6 wt %, less than 5 wt %, less than 4 wt %, less than 3 wt %, less than 2 wt %, or less than 1 wt % hydrogen bonding units. In some aspects, the polymeric material further comprises a thermal initiator, a second polymer, a crosslinking moiety, or a combination thereof.

In some aspects, the polymer comprises an aliphatic urethane (meth)acrylate. In some aspects, the polymeric material comprises isobornyl acrylate, isobornyl methacrylate, trimethylolpropane tri(meth)acrylate, 3,3,5-trimethcyclohexyl 2-((meth)acryloxy) benzoate, 3,3,5-Trimethylcyclohexyl (meth)acrylate, tripropylene glycol di(meth)acrylate, hexane-1,6-diol di(meth)acrylate, hydroxyethyl (meth)acrylate, benzyl (meth)acrylate, a derivative thereof, or a combination thereof. In some aspects, the polymer is hydrophobic. In some aspects, the polymeric material comprises 20-100 wt % of the polymer.

In some aspects, the polymeric material comprises the second polymer, and the wt % ratio of the polymer to the second polymer is from 100:1-1:100, from 50:1-1:50, from 40:1-1:40, from 30:1-1:30, from 25:1-1:25, from 20:1-1:20, from 15:1-1:15, from 10:1-1:10, from 5:1-1:5, from 4:1-1:4, from 3:1-1:3, from 2:1-1:2, 100:1 or less, 50:1 or less, 40:1 or less, 30:1 or less, 25:1 or less, 20:1 or less, 15:1 or less, 10:1 or less, 9:1 or less, 8:1 or less, 7:1 or less, 6:1 or less, 5:1 or less, 4:1 or less, 3:1 or less, 2:1 or less, or 1:1 or less.

In some aspects, the polymeric material comprises 0-50 wt % of the crosslinking moiety. In some aspects, the polymeric material comprises 30 wt % or less of the crosslinking moiety. In some aspects, the polymeric material comprises from 0 to 0.5 wt % of the thermal initiator. In some aspects, the thermal initiator comprises azobisisobutyronitrile, 2,2'-azodi(2-methylbutyronitrile), or a combination thereof.

In some aspects, the polymeric material is characterized by one or more of: an elongation at yield of greater than or equal to 4% at 24 hours testing in a wet environment at 37° C.; and an elongation at break of greater than 15% at 24 hours testing in a wet environment at 37° C. In some aspects, the polymeric material comprises less than 10 wt % water after 24 hours in a wet environment at 37° C. In some aspects, the polymeric material has an elongation at break greater than 15% after 24 hours in a wet environment at 37° C.

In some aspects, the polymeric material has an ultimate tensile strength from 10 MPa to 100 MPa, from 15 MPa to 80 MPa, from 20 MPa to 60 MPa, from 10 MPa to 50 MPa, from 10 MPa to 45 MPa, from 25 MPa to 40 MPa, from 30 MPa to 45 MPa, or from 30 MPa to 40 MPa after 24 hours in a wet environment at 37° C. In some aspects, the polymeric material has an ultimate tensile strength from 10 MPa to 50 MPa after 24 hours in a wet environment at 37° C. In some aspects, the polymeric material is characterized by a tensile modulus from 100 MPa to 3000 MPa or a tensile modulus from 800 MPa to 2000 MPa after 24 hours in a wet environment at 37° C. In some aspects, the polymeric material has a tensile modulus of greater than 200 MPa after 24 hours in a wet environment at 37° C. In some aspects, the polymeric material has a tensile modulus from 1.0 GPa to 1.4 GPa after 24 hours in a wet environment at 37° C. In some aspects, the polymeric material has a flexural stress remaining of greater than or equal to 10% after 24 hours in a wet environment at 37° C. In some aspects, the polymeric material is characterized by a flexural stress remaining of 5% to 45% of the initial load after 24 hours in a wet environment at 37° C., or a stress remaining of 20% to 45% of the initial load after 24 hours in a wet environment at 37° C. In some aspects, the polymeric material is characterized by a flexural stress remaining of 0.01 MPa to 15 MPa after 24 hours in a wet environment at 37° C., or a flexural stress remaining of 2 MPa to 15 MPa after 24 hours in a wet environment at 37° C. In some aspects, the polymeric material is characterized by an elongation at yield of 4% to 10%, or an elongation at yield of 5% to 10% after 24 hours in a wet environment at 37° C. In some aspects, the polymeric material is characterized by an elongation at break greater than 10%, an elongation at break greater than 20%, an elongation at break greater than 30%, an elongation at break of 5% to 250%, an elongation at break of 20% to 250%, or an elongation at break value between 40% and 250% after 24 hours in a wet environment at 37° C. In some aspects, the polymeric material is characterized by a tensile strength at yield greater than or equal to 5 MPa, a tensile strength at yield of 5 MPa to 85 MPa, or a tensile strength at yield of 10 MPa to 55 MPa after 24 hours in a wet environment at 37° C. In some aspects, the polymeric material is characterized by a storage modulus of 0.1 MPa to 4000 MPa, a storage modulus of 300 MPa to 3000 MPa, or a storage modulus of 750 MPa to 3000 MPa after 24 hours in a wet environment at 37° C. In some aspects, the polymeric material has a flexural stress remaining of 80 MPa or less, 70 MPa or less, 60 MPa or less, or 50 MPa or less after 24 hours in a wet environment at 37° C. In some aspects, the polymeric material has a flexural stress remaining of 80 MPa or less, 70 MPa or less, 60 MPa or less, or 50 MPa or less after a time period of use. In some aspects, the time period of use is 1 minute, 5 minutes, 10 minutes, 30 minutes, 1 hour, or 24 hours. In some aspects, the polymeric material has a maximum force at 5% strain greater than 3 pound-force per 3.57 $cm^2$. In some aspects, the polymeric material has a remaining force greater than 0.1 pound-force per 3.57 $cm^2$ after being submerged for 24 hours in a wet environment having a temperature of 37° C.

In some aspects, greater than 70% of visible light passes through the polymeric material after 24 hours in a wet environment at 37° C. In some aspects, the polymeric material is biocompatible, bioinert, or a combination thereof.

In various aspects, the present disclosure provides an orthodontic appliance comprising the polymeric material disclosed herein. In various aspects, the present disclosure provides an orthodontic appliance formed from the photo-curable resin disclosed herein. In various aspects, the present disclosure provides an orthodontic appliance formed using the methods disclosed herein.

In some aspects, the orthodontic appliance is an aligner, expander or spacer. In some aspects, he orthodontic appliance comprises a plurality of tooth receiving cavities configured to reposition teeth from a first configuration toward a second configuration. In some aspects, the orthodontic appliance is one of a plurality of orthodontic appliances configured to reposition the teeth from an initial configuration toward a target configuration. In some aspects, the orthodontic appliance is one of a plurality of orthodontic appliances configured to reposition the teeth from an initial configuration toward a target configuration according to a treatment plan. In some aspects, the orthodontic appliance is an aligner.

In various aspects, the present disclosure provides a method of forming a polymeric material, the method comprising: providing the photo-curable resin disclosed herein; and curing the photo-curable resin, forming the polymeric material disclosed herein.

In various aspects, the present disclosure provides a method of repositioning a patient's teeth, the method comprising: generating a treatment plan for a patient, the plan comprising a plurality of intermediate tooth arrangements for moving teeth along a treatment path from an initial arrangement toward a final arrangement; producing a 3D printed orthodontic appliance comprising less than or equal to 10 wt % hydrogen bonding units; and moving on-track, with the orthodontic appliance, at least one of the patient's teeth toward an intermediate arrangement or a final tooth arrangement.

In some aspects, the method further comprises tracking progression of the patient's teeth along the treatment path after administration of the orthodontic appliance, the tracking comprising comparing a current arrangement of the patient's teeth to a planned arrangement of the teeth. In some aspects, greater than 60% of the patient's teeth are on track with the treatment plan after 2 weeks of treatment. In some aspects, the method further comprises achieving on-track the movement of the at least one of the patient's teeth to the intermediate arrangement or the final tooth arrangement. In some aspects, prior to moving on-track, with the orthodontic appliance, the at least one of the patient's teeth toward the intermediate arrangement or the final tooth arrangement, the orthodontic appliance comprises a first flexural stress; and after achieving on-track the movement of the at least one of the patient's teeth to the intermediate arrangement or the final tooth arrangement, the orthodontic appliance comprises a second flexural stress.

In some aspects, the producing comprises direct fabrication, and optionally wherein the direct fabrication comprises cross-linking the photo-curable resin. In some aspects, the 3D printed orthodontic appliance is the orthodontic appliance as disclosed herein.

In various aspects, the present disclosure provides a method of forming a polymeric material, the method comprising: providing the photo-curable resin disclosed herein; and producing a product, wherein producing the product comprises additive manufacturing.

In some aspects, the polymeric material disclosed herein is formed from the photo-curable resin disclosed herein with additive manufacturing.

In various aspects, the present disclosure provides a polymeric material prepared by a process comprising: providing the photo-curable resin disclosed herein; and forming the polymeric material from the photo-curable resin with additive manufacturing.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE INVENTION

Figure 1A:
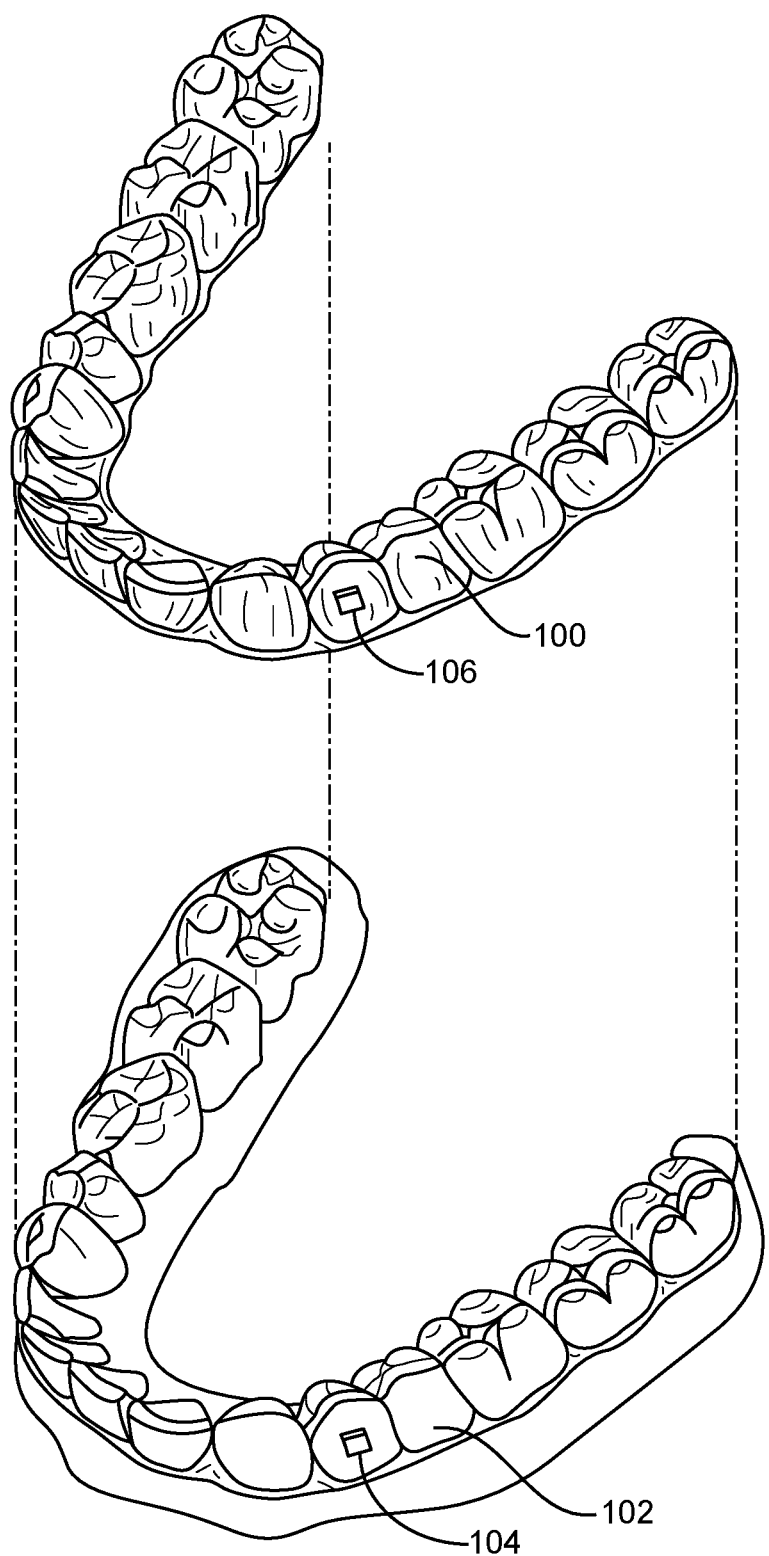
FIG. 1A illustrates a tooth repositioning appliance, in accordance with embodiments.

The present disclosure provides low-viscosity resins for producing polymers with properties suitable for use in various mechanical appliances, such as orthodontic appliances (e.g., aligners). The low-viscosity resins may be photo-curable and can be used with direct fabrication methods and equipment. In various embodiments, the polymeric materials produced from the low-viscosity resins described herein have high toughness while remaining resistant to stress relaxation. Low-viscosity, photo-curable resins described herein have reduced hydrogen bonding in comparison to traditional materials (e.g., materials having high urethane content) used in orthodontic appliances. By using reduced hydrogen bonding density in the resins of the present disclosure, it is possible to incorporate higher molecular weight materials while maintaining relatively low viscosity, which results in a material that can be produced by direct fabrication and having favorable mechanical properties.

Photo-Curable Resins

In some embodiments, the present disclosure provides photo-curable resins (i.e., resins that undergo light-activated polymerization). The photo-curable resins comprise an oligomer and an initiator. In some embodiments, the photo-curable resins comprise an oligomer having a number-average molecular weight of greater than or equal to 3,000 Da, greater than or equal to 4,000 Da, greater than or equal to 5,000 Da, greater than or equal to 6,000 Da, greater than or equal to 7,000 Da, greater than or equal to 8,000 Da, greater than or equal to 9,000 Da, or greater than or equal to 10,000 Da. In some embodiments, the photo-curable resins comprise an oligomers having a number-average molecular weight of less than 30,000 Da, less than 25,000 Da, less than 20,000 Da, less than 15,000 Da, less than 10,000 Da, or less than 5,000 Da. In some embodiments the oligomer has a number-average molecular weight from 3,000 Da to 10,000 Da, from 3,000 Da to 9,000 Da, from 3,000 Da to 8,000 Da, or from 3,000 Da to 7,000 Da. In preferred embodiments, the photo-curable resin comprises an oligomer having a number-average molecular weight of greater than 3,000 Da. In some preferred embodiments, the number-average molecular weight of the oligomer is from 9,000 Da to 20,000 Da. In some embodiments, the photo-curable resins comprise an oligomer comprising a plurality of monomers. In certain embodiments, the average chain length of the oligomer is from 20 to 200 monomers. In some embodiments, the oligomer comprises a plurality of repeating units (e.g., repeating monomers). In some embodiments, the oligomer comprises a backbone that consists or consists essentially of repeating units. In some embodiments, the oligomer comprises from 20 to 200 repeating units.

In some embodiments, the oligomer comprises an aliphatic urethane acrylate, an aliphatic urethane methacrylate, or a combination thereof. In some embodiments, the oligomer comprises a hydrophobic urethane acrylate, a hydrophobic urethane methacrylate, or a combination thereof. In some embodiments, the oligomer comprises a polybutadiene urethane acrylate, a polybutadiene urethane methacrylate, or a combination thereof. In some embodiments, the oligomer comprises a polyether urethane acrylate, a polyether urethane methacrylate, or a combination thereof. In some embodiments, the oligomer comprises Dymax BRC-4421, Dymax BR-543, Dymax BR-543 MB, Exothane 108, Exothane 10, isophorone urethane dimethacrylate (IPDI-UDMA), CN991, CN9782, CN3211, CN9782, CN9009, PU3201NT, an acrylate thereof, a methacrylate thereof, or a combination thereof. In some embodiments, the oligomer is an aliphatic urethane diacrylate, an aliphatic urethane dimethacrylate, or a combination thereof.

In some embodiments, the oligomer comprises two or more functional groups. In certain embodiments, the oligomer is difunctional. In other embodiments, the oligomer is monofunctional. In certain embodiments, the photo-curable resin comprises a plurality of oligomers, and wherein the plurality of oligomers comprise a monofunctional oligomer, a difunctional oligomer, a multifunctional oligomer, or a combination thereof. In certain embodiments, the oligomer is not functionalized with reactive groups. In some embodiments wherein the oligomer has a high number-average molecular weight, the oligomer is not functionalized with reactive groups. In some embodiments, the oligomer has a number-average molecular weight greater than 15 kDa and is not functionalized with a reactive group.

In some embodiments, the oligomer comprises at least one reactive functional group. In certain embodiments, the reactive functional groups allow for further modification of the oligomer and/or formed polymer, such as additional polymerization. In some embodiments, the oligomer comprises 1, 2, 3, 4, 5, 6, 7, 8, 9, 10, or more than 10 reactive functional groups. The reactive functional groups can be the same, or they can be of different functionality. In some embodiments, the oligomer is a telechelic polymer (i.e., a polymer having di-end functionalization, wherein both ends have the same functionality). In some embodiments, the one or more functional groups are at the terminal end(s) of the oligomer. In some embodiments, the one or more reactive functional groups are located at positions other than the terminal end(s) of the oligomer (e.g., in-chain and/or pendant functional groups). In some embodiments, the oligomer comprises a plurality of reactive functional groups, and the reactive functional groups are located at one or both terminal ends of the oligomer, in-chain, at a pendant (e.g., a side group attached to the polymer backbone), or any combination thereof. In some embodiments, the plurality of reactive functional groups are the same. In other embodiments, the plurality of reactive functional groups are different from one another. In some embodiments, the plurality of reactive functional groups comprises at least two functional groups that are the same.

Non-limiting examples of reactive functional groups include free radically polymerizable functionalities, photoactive groups, groups facilitating step growth polymerization, thermally reactive groups, and/or groups that facilitate bond formation (e.g., covalent bond formation). In some embodiments, the functional groups comprise an acrylate, a methacrylate, an acrylamide, a vinyl group, a vinyl ether, a vinyl ester, a thiol, an allyl ether, a norbornene, a vinyl acetate, a maleate, a fumarate, a maleimide, an epoxide, a ring-strained cyclic ether, a ring-strained thioether, a cyclic ester, a cyclic carbonate, a cyclic silane, a cyclic siloxane, a hydroxyl, an amine, an isocyanate, a blocked isocyanate, an acid chloride, an activated ester, a Diels-Alder reactive group, a furan, a cyclopentadiene, an anhydride, a group favorable toward photodimerization (e.g., an anthracene, an acenaphthalene, or a coumarin), a group that photodegrades into a reactive species (e.g., Norrish Type 1 and 2 materials), an azide, a derivative thereof, or a combination thereof.

In some embodiments, the photo-curable resins comprise a low percentage of hydrogen bonding units. In certain embodiments, the photo-curable resin has a low amount of hydrogen bonding. The photo-curable resin can have less than 40 wt %, less than 35 wt %, less 30 wt %, than less than 25 wt %, less than 20 wt %, less than 15 wt %, less than 14 wt %, less than 13 wt %, less than 12 wt %, less than 11 wt %, less than 10 wt %, less than 9 wt %, less than 8 wt %, less than 7 wt %, less than 6 wt %, less than 5 wt %, less than 4 wt %, less than 3 wt %, less than 2 wt %, or less than 1 wt % hydrogen bonding units (e.g., urethanes, ureas, amides, hydroxyls, amines, carbonyl-based acids, phosphorous-based acids, sulfur-based acids, Poly(ethylene glycol) ethers, and derivatives thereof). The percentage of hydrogen bonding units can preferably be calculated or measured by weight percentage of hydrogen bonding groups. As a non-limiting example, the NHCO of an amide bond acts as both hydrogen donor and hydrogen acceptor; accordingly, a photo-curable resin having less than 15 wt % of the NHCO unit (and no other type of hydrogen bonding units) has less than 15 wt % hydrogen bonding units. Alternatively, in some systems, the value of wt % hydrogen bonding units can be determined by performing titration to obtain the number of hydrogen bonding groups. In preferred embodiments, the photo-curable resin comprises less than 20 wt % hydrogen bonding units.

In some embodiments, the photo-curable resin comprises 0.5-99.5 wt % of the oligomer, 1-99 wt % of the oligomer, 10-95 wt % of the oligomer, 20-90 wt % of the oligomer, 25-60 wt % of the oligomer, or 35-50 wt % of the oligomer. In preferred embodiments, the photo-curable resin comprises 25-60 wt % of the oligomer. In some preferred embodiments, the photo-curable resin comprises 99.5 wt % or less of the oligomer.

In some embodiments, the photo-curable resins have a low viscosity at ambient temperatures. In some embodiments, the photo-curable resin has a viscosity less than or equal to 30,000 cP, less than or equal to 25,000 cP, less than or equal to 20,000 cP, less than or equal to 19,000 cP, less than or equal to 18,000 cP, less than or equal to 17,000 cP, less than or equal to 16,000 cP, less than or equal to 15,000 cP, less than or equal to 14,000 cP, less than or equal to 13,000 cP, less than or equal to 12,000 cP, less than or equal to 11,000 cP, less than or equal to 10,000 cP, less than or equal to 9,000 cP, less than or equal to 8,000 cP, less than or equal to 7,000 cP, less than or equal to 6,000 cP, or less than or equal to 5,000 cP at 25° C. The dynamic viscosity of a fluid indicates its resistance to shearing flows. The SI unit for dynamic viscosity is the Poiseuille (Pa·s). Dynamic viscosity is commonly given in units of centipoise, where 1 centipoise (cP) is equivalent to 1 mPa·s. Kinematic viscosity is the ratio of the dynamic viscosity to the density of the fluid; the SI unit is $m^2$/s. Devices for measuring viscosity include viscometers and rheometers. The viscosity of a composition described herein may be measured at various temperatures using a rheometer. For example, a Discovery HR-2 rheometer from TA Instruments may be used for rheological measurement in rotation mode (40 mm parallel plate, 200 μm gap, 4 $s^{-1}$). In preferred embodiments, the resin has a viscosity less than 15,000 cP at 25° C.

In some embodiments, the photo-curable resin has a viscosity less than or equal to 100,000 cP, less than or equal to 90,000 cP, less than or equal to 80,000 cP, less than or equal to 70,000 cP, less than or equal to 60,000 cP, less than or equal to 50,000 cP, less than or equal to 40,000 cP, less than or equal to 35,000 cP, less than or equal to 30,000 cP, less than or equal to 25,000 cP, less than or equal to 20,000 cP, less than or equal to 15,000 cP, less than or equal to 10,000 cP, less than or equal to 5,000 cP, less than or equal to 4,000 cP, less than or equal to 3,000 cP, less than or equal to 2,000 cP, less than or equal to 1,000 cP, less than or equal to 750 cP, less than or equal to 500 cP, less than or equal to 250 cP, less than or equal to 100 cP, less than or equal to 90 cP, less than or equal to 80 cP, less than or equal to 70 cP, less than or equal to 60 cP, less than or equal to 50 cP, less than or equal to 40 cP, less than or equal to 30 cP, less than or equal to 20 cP, or less than or equal to 10 cP at a printing temperature. In some embodiments, the photo-curable resin has a viscosity from 50,000 cP to 30 cP, from 40,000 cP to 30 cP, from 30,000 cP to 30 cP, from 20,000 cP to 30 cP, from 10,000 cP to 30 cP, or from 5,000 cP to 30 cP at a printing temperature. In some embodiments, the printing temperature is from 0° C. to 25° C., from 25° C. to 40° C., from 40° C. to 100° C., or from 20° C. to 150° C. In preferred embodiments, the photo-curable resin has a viscosity from 30 cP to 50,000 cP at a printing temperature, wherein the printing temperature is from 20° C. to 150° C.

In preferred embodiments, the photo-curable resin has a viscosity less than 20,000 cP at a print temperature. In some embodiments, the print temperature is from 10° C. to 200° C., from 15° C. to 175° C., from 20° C. to 150° C., from 25° C. to 125° C., or from 30° C. to 100° C. In preferred embodiments, the print temperature is from 20° C. to 150° C.

In certain embodiments, the photo-curable resin has a viscosity less than 1,000 cP at 110° C. In some embodiments, the photo-curable resin has a viscosity less than 1,000 cP at 90° C. In some embodiments, the photo-curable resin has a viscosity less than 500 cP at 70° C. In some embodiments, the photo-curable resin has a viscosity less than 200 cP at 90° C. In some embodiments, the photo-curable resin has a viscosity less than 10,000 cP at 25° C.

In some embodiments, the photo-curable resins comprise an initiator that is a photoinitiator. Photoinitiators may be useful for various purposes, including for curing of polymers, including those that can be activated with light and initiate polymerization of the polymerizable components of the formulation. In embodiments, the photoinitiator is a radical photoinitiator and/or a cationic initiator. In some embodiments, the photoinitiator is a Type I photoinitiator which undergoes a unimolecular bond cleavage to generate free radicals. In an additional embodiment the photoinitiator is a Type II photoinitiator which undergoes a bimolecular reaction to generate free radicals. Common Type I photoinitiators include, but are not limited to benzoin ethers, benzil ketals, α-dialkoxy-acetophenones, α-hydroxy-alkyl phenones and acyl-phosphine oxides. Common Type II photoinitiators include benzophenones/amines and thioxanthones/amines. Cationic initiators include aryldiazonium, diaryliodonium, and triarylsulfonium salts. In preferred embodiments, the photoinitiator comprises diphenyl (2,4,6-trimethylbenzoyl)-phosphine oxide, ethyl (2,4,6-trimethylbenzoyl) phenyl phosphinate, or a combination thereof. In certain preferred embodiments, the photoinitiator comprises a radical photoinitiator, a cationic initiator, and/or a photobase generator. In some preferred embodiments, the photoinitiator is a Type I photoinitiator which undergoes a unimolecular bond cleavage to generate free radicals, or a Type II photoinitiator which undergoes a bimolecular reaction to generate free radicals. In some preferred embodiments, the Type I photoinitiator is a benzoin ether, a benzil ketal, an α-dialkoxy-acetophenone, an α-hydroxy-alkyl phenome, or an acyl-phosphine oxide. In some preferred embodiments, the Type II photoinitiator is a benzophenone/amine or a thioxanthone/amine. In some preferred embodiments, the cationic initiators is an aryldiazonium, a diaryliodonium, or a triarylsulfonium salt.

In some embodiments, the photoinitiator initiates photopolymerization using light energy. In certain embodiments, the photoinitiator initiates photopolymerization with exposure to light energy from 800 nm to 250 nm, from 800 nm to 350 nm, from 800 nm to 450 nm, from 800 nm to 550 nm, from 800 nm to 650 nm, from 600 nm to 250 nm, from 600 nm to 350 nm, from 600 nm to 450 nm, or from 400 nm to 250 nm. In some embodiments, the photoinitiator initiates photopolymerization following absorption of two photons, which can use longer wavelengths of light to initiate the photopolymerization.

In some embodiments, the resin comprises more than one initiator (e.g., 2, 3, 4, 5, or more than 5 initiators). In some embodiments, the photo-curable resins comprise an initiator that is a thermal initiator. In certain embodiments, the thermal initiator comprises an organic peroxide. In some embodiments, the thermal initiator comprises an azo compound, an inorganic peroxide, an organic peroxide, or any combination thereof. In some embodiments, the thermal initiator is selected from the group consisting of tert-amyl peroxybenzoate, 4,4-azobis(4-cyanovaleric acid), 1,1'-azobis(cyclohexanecarbonitrile), 2,2'-azobisisobutyronitrile (AIBN), benzoyl peroxide, 2,2-bis(tert-butylperoxy)butane, 1,1-bis(tert-butylperoxy)cyclohexane, 2,5-bis(tert-butylperoxy 2,5-dimethylhexane, 2,5-bis(tert-butylperoxy)-2,5-dimethyl-3-hexyne, bis(1-(tert-butylperoxy)-3,3,5-trimethylcyclohexane, tert-butyl hydroxyperoxide, tert-butyl peracetate, tert-butyl peroxide, tert-butyl peroxybenzoate, tert-butylperoxy isopropyl carbonate, cumene hydroperoxide, cyclohexanone peroxide, dicumyl peroxide, lauroyl peroxide, 2,4-pentanedione peroxide, peracetic acid, potassium persulfate, a derivative thereof, and a combination thereof. In preferred embodiments, the thermal initiator comprises azobisisobutyronitrile, 2,2'-azodi(2-methylbutyronitrile), or a combination thereof.

In some embodiments, the photo-curable resin comprises 0.01-10 wt %, 0.02-5 wt %, 0.05-4 wt %, 0.1-3 wt %, 0.1-2 wt %, or 0.1-1 wt % of the initiator. In preferred embodiments, the photo-curable resin comprises 0.1-2 wt % of the initiator. In some embodiments, the photo-curable resin comprises 0.01-10 wt %, 0.02-5 wt %, 0.05-4 wt %, 0.1-3 wt %, 0.1-2 wt %, or 0.1-1 wt % of the photoinitiator. In preferred embodiments, the photo-curable resin comprises 0.1-2 wt % of the photoinitiator. In some embodiments, the photo-curable resin comprises from 0 to 10 wt %, from 0 to 9 wt %, from 0 to 8 wt %, from 0 to 7 wt %, from 0 to 6 wt %, from 0 to 5 wt %, from 0 to 4 wt %, from 0 to 3 wt %, from 0 to 2 wt %, from 0 to 1 wt %, or from 0 to 0.5 wt % of the thermal initiator. In preferred embodiments, the photo-curable resin comprises from 0 to 0.5 wt % of the thermal initiator.

In some preferred embodiments, the present disclosure provides photo-curable resins comprising: an oligomer having a number-average molecular weight of greater than 3,000 Da; and an initiator, wherein the photo-curable resin comprises less than 20 wt % hydrogen bonding units and has a viscosity less than or equal to 15,000 cup at 25° C. In some preferred embodiments, the present disclosure provides photo-curable resins comprising: an oligomer having a number-average molecular weight of greater than 3,000 Da; and a photoinitiator, wherein the photo-curable resin comprises less than 10 wt % hydrogen bonding units.

In some embodiments, the photo-curable resins are capable of being 3D printed (i.e., can be used in additive manufacturing).

Additional Components of Photo-Curable Resins

In some embodiments, the photo-curable resins further comprise a reactive diluent. A "reactive diluent" as used herein refers to a substance which reduces the viscosity of another substance, such as a monomer or a curable resin. A reactive diluent may become part of another substance, such as a polymer obtained by a polymerization process. In some embodiments, a reactive diluent is a curable monomer which, when mixed with a photo-curable resin, reduces the viscosity of the resultant formulation and is incorporated into the polymer that results from polymerization of the formulation. The reactive diluent typically has a low viscosity. One or more reactive diluents may be included in the composition to reduce the viscosity of the photo-curable resin, e.g., to a viscosity less than the viscosity of the photo-curable resin in the absence of the reactive diluent. In some embodiments, the reactive diluent has a viscosity lower than the viscosity of the oligomer. In some embodiments, the reactive diluent may reduce the viscosity of the photo-curable resin. The reactive diluent or reactive diluents may reduce the viscosity of the photo-curable resin by at least 10%, at least 20%, at least 30%, at least 40%, at least 50%, at least 60%, at least 70%, at least 80%, or at least 90%. In some embodiments, the reactive diluent or reactive diluents have a melting point lower than the processing temperatures disclosed herein. In some embodiments, the reactive diluent or reactive diluents have a melting point less than 120° C., less than 110° C., less than 100° C., less than 90° C., less than 80° C., less than 70° C., less than 60° C., less than 50° C., less than 40° C., or less than 30° C. In some embodiments, the photo-curable resin comprises 10-75 wt % of the reactive diluent, 15-60 wt % of the reactive diluent, 20-50 wt % of the reactive diluent, 25-45 wt % of the reactive diluent, or 30-40 wt % of the reactive diluent. In some preferred embodiments, the photo-curable resin comprises 30-70 wt % of the reactive diluent. In some embodiments, the photo-curable resins further comprise a cross-linking modifier. In certain embodiments, the reactive diluent comprises a crosslinking modifier. In some embodiments, a crosslinking modifier comprises the reactive diluent.

In some embodiments, the reactive diluent comprises an acrylate, a methacrylate, or a combination thereof. As used herein, a "(meth)acrylate" (and variations thereof) is an acrylate, a methacrylate, or a combination thereof. Similarly, terms such as "di(meth)acrylate) is a diacrylate, a dimethacrylate, or a combination thereof; "(meth)acryloxy" is an acryloxy, a methacryloxy, or a combination thereof; "tri (meth)acrylate" is a triacrylate, a trimethacrylate, or a combination thereof. As a non-limiting example, hydrobenzoic acid ester (meth)acrylate is understood to be hydrobenzoic acid ester acrylate, hydrobenzoic acid ester methacrylate, or a combination thereof. In some embodiments, the reactive diluent comprises a (meth)acrylate, a di(meth)acrylate, a di(meth)acrylate of polyglycols, a hydrobenzoic acid ester (meth)acrylate, a cycloalkyl-2-, 3-, or 4-((meth)acryloxy) benzoate, isobornyl (meth)acrylate, trimethylolpropane tri (meth)acrylate, triethylene glycol di(meth)acrylate (e.g., TEGDMA), 1,12-dodecanediol di(meth)acrylate (e.g., D4MA), 3,3,5-trimethcyclohexyl 2-((meth)acryloxy) benzoate (e.g., HSMA), benzyl salicylate (meth)acrylate (e.g., BSMA), 3,3,5-Trimethylcyclohexyl (meth)acrylate, tripropylene glycol di(meth)acrylate, hexane-1,6-diol di(meth) acrylate, tricyclodecanedimethanol di(meth)acrylate, tricyclodecanedimethanol di(meth)acrylate, hydroxyethyl (meth) acrylate, benzyl (meth)acrylate, a (poly)vinyl monomer, a derivative thereof, or a combination thereof.

In some embodiments, the reactive diluent comprises an acrylate or methacrylate. In some embodiments, the reactive diluent comprises a (poly)glycol di(meth)acrylate, a triethylene glycol di(meth)acrylate, a tetraethylene glycol di(meth)acrylate, bisphenol A di(meth)acrylate, a hydrogenated form of bisphenol A di(meth)acrylate, a methacrylate- or acrylate-terminated polyester oligomer, 4,4'-isopropylidenedicyclohexanol di(meth)acrylate, a salicylic ester (meth)acrylate, or cycloalkyl salicylate (meth)acrylate. In certain embodiments, the reactive diluent comprises a (poly) vinyl monomer. In certain embodiments, the reactive diluent comprises vinyl acetate, styrene, or divinylbenzene.

In some embodiments, the reactive diluent comprises a functional group selected from polyurethane, acrylate, methacrylate, vinyl ester, epoxy, and combinations thereof. As examples, the reactive diluent is an acrylate, epoxy or urethane based diluent. In some embodiments, the reactive diluent is a vinyl monomer or a thiol monomer. As examples, the reactive diluent is selected from the group consisting of diacrylate monomers, triacrylate monomers, acyclic diacrylate monomers, cyclic diacrylate monomers, methacrylate monomers, vinyl ester monomers, polyurethane monomers with acrylate end groups and polyurethane monomers with epoxy end groups. In some embodiments, the reactive diluent is selected from the group consisting of 1-vinyl-2-pyrrolidinone (NVP), CEA (β-carboxyethylacrylate), trimethyl cyclohexyl acrylate (M1130), isobornyl acrylate (IBOA), Isobornyl methacrylate (IBOMA), tetrahydrofurfuryl methacrylate (M151), PETMP, TATATO, and any combination thereof. In some embodiments, the viscosity of the reactive diluent is less than the viscosity of other oligomer components in the formulation. In some embodiments, the viscosity of the reactive diluent is less than the viscosity of the crosslinking modifier.

In some embodiments, the photo-curable resin further comprises a crosslinking modifier. A "crosslinking modifier" as used herein refers to a substance which bonds one oligomer or polymer chain to another oligomer or polymer chain, thereby forming a crosslink. A crosslinking modifier may become part of another substance, such as a crosslink in a polymer material obtained by a polymerization process. In some embodiments, a crosslinking modifier is a curable unit which, when mixed with a photo-curable resin, is incorporated as a crosslink into the polymeric material that results from polymerization of the formulation. In certain embodiments, the photo-curable resin comprises 0-25 wt % of the crosslinking modifier, the crosslinking modifier having a number-average molecular weight equal to or less than 3,000 Da, equal to or less than 2,500 Da, equal to or less than 2,000 Da, equal to or less than 1,500 Da, equal to or less than 1,250 Da, equal to or less than 1,000 Da, equal to or less than 800 Da, equal to or less than 600 Da, or equal to or less than 400 Da. In some embodiments, the crosslinking modifier can have a high glass transition temperature ($T_g$), which leads to a high heat deflection temperature. In some embodiments, the crosslinking modifier has a glass transition temperature greater than −10° C., greater than −5° C., greater than 0° C., greater than 5° C., greater than 10° C., greater than 15° C., greater than 20° C., or greater than 25° C. In some preferred embodiments, the photo-curable resin comprises 0-25 wt % of the crosslinking modifier, the crosslinking modifier having a number-average molecular weight equal to or less than 1,500 Da. In some embodiments, the crosslinking modifier comprises a (meth)acrylate-terminated polyester, a tricyclodecanediol di(meth)acrylate, a vinyl ester-terminated polyester, a tricyclodecanediol vinyl ester, a derivative thereof, or a combination thereof.

In some embodiments, the photo-curable resin further comprises a crosslinking modifier, a light blocker, a solvent, a glass transition temperature modifier, or a combination thereof. In some embodiments, the photo-curable resin further comprises a polymerization catalyst, a polymerization inhibitor, a light blocker, a plasticizer, a solvent, a surface energy modifier (e.g., a mold releasing agent), a pigment, a dye, a filler, a biologically significant chemical, or any combination thereof.

In some embodiments, the photo-curable resin comprises a polymerization catalyst. In some embodiments, the polymerization catalyst comprises a tin catalyst, a platinum catalyst, a rhodium catalyst, a titanium catalyst, a silicon catalyst, a palladium catalyst, a metal triflate catalyst, a boron catalyst, a bismuth catalyst, or any combination thereof. Non-limiting examples of a titanium catalyst include di-n-butylbutoxychlorotin, di-n-butyldiacetoxytin, di-n-butyldilauryltin, dimethyldineodecanoatetin, dioctyldilauryltin, tetramethyltin, and dioctylbis(2-ethylhexylmaleate)tin. Non-limiting examples of a platinum catalyst include platinum-divinyltetramethyl-disiloxane complex, platinum-cyclovinylmethyl-siloxane complex, platinum-octanal complex, and platinum carbonyl cyclovinylmethylsiloxane complex. A non-limiting example of a rhodium catalyst includes tris(dibutylsulfide)rhodium trichloride. Non-limiting examples of a titanium catalyst includes titaium isopropoxide, titanium 2-ethyl-hexoxide, titanium chloride triisopropoxide, titanium ethoxide, and titanium diisopropoxide bis(ethylacetoacetate). Non-limiting examples of a silicon catalyst include tetramethylammonium siloxanolate and tetramethylsilylmethyl-trifluoromethanesulfonate. A non-limiting example of a palladium catalyst includes tetrakis(triphenylphosphine)palladium(0). Non-limiting examples of a metal triflate catalyst include scandium trifluoromethanesulfonate, lanthanum trifluoromethanesulfonate, and ytterbium trifluoromethanesulfonate. A non-limiting example of a boron catalyst includes tris(pentafluorophenyl) boron. Non-limiting examples of a bismuth catalyst include bismuth-zinc neodecanoate, bismuth 2-ethylhexanoate, a metal carboxylate of bismuth and zinc, and a metal carboxylate of bismuth and zirconium.

In some embodiments, the photo-curable resin comprises a polymerization inhibitor in order to stabilize the composition and prevent premature polymerization. In some embodiments, the polymerization inhibitor is a photopolymerization inhibitor (e.g., oxygen). In some embodiments, the polymerization inhibitor is a phenolic compound (e.g., BHT). In some embodiments, the polymerization inhibitor is a stable radical (e.g., 2,2,4,4-tetramethylpiperidinyl-1-oxy radical, 2,2-diphenyl-1-picrylhydrazyl radical, galvinoxyl radical, or triphenylmethyl radical). In some embodiments, more than one polymerization inhibitor is present in the resin. In some embodiments, the polymerization inhibitor acts as a radical scavenger. In certain embodiments, the polymerization inhibitor is an antioxidant, a hindered amine light stabilizer (HAL), a hindered phenol, or a deactivated radical (e.g., a peroxy compound). In some embodiments, the polymerization inhibitor is selected from the group consisting of 4-tert-butylpyrocatechol, tert-butylhydroquinone, 1,4-benzoquinone, 6-tert-butyl-2,4-xylenol, 2-tert-butyl-1,4-benzoquinone, 2,6-di-tert-butyl-p-cresol, 2,6-di-tert-butylphenol, 1,1-diphenyl-2-picrylhydrazyl free radical, hydroquinone, 4-methoxyphenol, phenothiazine, any derivative thereof, and any combination thereof.

In some embodiments, the photo-curable resin comprises a light blocker in order to dissipate UV radiation. In some embodiments, the light blocker absorbs a specific UV energy value and/or range. In some embodiments, the light blocker is a UV light absorber, a pigment, a color concentrate, or an IR light absorber. In some embodiments, the light blocker comprises a benzotriazole (e.g., 2-(2'-hydroxy-phenyl benzotriazole), 2,2'-dihydroxy-4-methoxybenzophenone, 9,10-diethoxyanthracene, a hydroxyphenyltriazine, an oxanilide, a benzophenone, or a combination thereof. In some embodiments, the photo-curable resin comprises from 0 to 10 wt %, from 0 to 9 wt %, from 0 to 8 wt %, from 0 to 7 wt %, from 0 to 6 wt %, from 0 to 5 wt %, from 0 to 4 wt %, from 0 to 3 wt %, from 0 to 2 wt %, from 0 to 1 wt %, or from 0 to 0.5 wt % of the light blocker. In preferred embodiments, the photo-curable resin comprises from 0 to 0.5 wt % of the light blocker.

In some embodiments, the photo-curable resin comprises a filler. In some embodiments, the filler comprises calcium carbonate (i.e., chalk), kaolin, metakolinite, a kaolinite derivative, magnesium hydroxide (i.e., talc), calcium silicate (i.e., wollastonite), a glass filler (e.g., glass beads, short glass fibers, or long glass fibers), a nanofiller (e.g., nanoplates, nanofibers, or nanoparticles), a silica filler (e.g., a mica, silica gel, fumed silica, or precipitated silica), carbon black, dolomite, barium sulfate, ATH $Al(OH)_3$, MDH $Mg(OH)_2$, diatomaceous earth, magnetite, halloysite, zinc oxide, titanium dioxide, cellulose, lignin, a carbon filler (e.g., chopped carbon fiber or carbon fiber), a derivative thereof, or a combination thereof.

In some embodiments, the photo-curable comprises a pigment, a dye, or a combination thereof. A pigment is typically a suspended solid that may be insoluble in the resin. A dye is typically dissolved in the photo-curable resin. In some embodiments, the pigment comprises an inorganic pigment. In some embodiments, the inorganic pigment comprises an iron oxide, barium sulfide, zinc oxide, antimony trioxide, a yellow iron oxide, a red iron oxide, ferric ammonium ferrocyanide, chrome yellow, carbon black, or aluminum flake. In some embodiments, the pigment comprises an organic pigment. In some embodiments, the organic pigment comprises an azo pigment, an anthraquinone pigment, a copper phthalocyanine (CPC) pigment (e.g., phthalo blue or phthalo green) or a combination thereof. In some embodiments, the dye comprises an azo dye (e.g., a diarylide or Sudan stain), an anthraquinone (e.g., Oil Blue A or Disperse Red 11), or a combination thereof.

In some embodiments, the photo-curable resin comprises a surface energy modifier. In some embodiments, the surface energy modifier can aid the process of releasing a polymer from a mold. In some embodiments, the surface energy modifier can act as an antifoaming agent. In some embodiments, the surface energy modifier comprises a defoaming agent, a deairation agent, a hydrophobization agent, a leveling agent, a wetting agent, or an agent to adjust the flow properties of the photo-curable resin. In some embodiments, the surface energy modifier comprises an aloxylated surfactant, a silicone surfactant, a sulfosuccinate, a fluorinated polyacrylate, a fluoropolymer, a silicone, a star-shaped polymer, an organomodified silicone, or any combination thereof.

In some embodiments, the photo-curable resin comprises a plasticizer. A plasticizer can be a nonvolatile material that can reduce interactions between polymer chains, which can decrease glass transition temperature, melt viscosity, and elastic modulus. In some embodiments, the plasticizer comprises a dicarboxylic ester plasticizer, a tricarboxylic ester plasticizer, a trimellitate, an adipate, a sebacate, a maleate, or a bio-based plasticizer. In some embodiments, the plasticizer comprises a dicarboxylic ester or a tricarboxylic ester comprising a dibasic ester, a phthalate, bis(2-ethylhexyl) phthalate (DEHP), bis(2-propylheptyl) phthalate (DPHP), diisononyl phthalate (DINP), di-n-butyl phthalate (DBP), butyl benzyl phthalate (BBzP), diisodecyl phthalate (DIDP), dioctyl phthalate (DOP), diisooctyl phthalate (DIOP), diethyl phthalate (DEP), diisobutyl phthalate (DIBP), di-n-hexyl phthalate, a derivative thereof, or a combination thereof. In some embodiments, the plasticizer comprises a trimellitate comprising trimethyl trimellitate (TMTM), tri-(2-ethylhexyl) trimellitate (TEHTM), tri-(n-octyl,n-decyl) trimellitate (ATM), tri-(heptyl,nonyl) trimellitate (LTM), n-octyl trimellitate (OTM), trioctyl trimellitate, a derivative thereof, or a combination thereof. In some embodiments, the plasticizer comprises an adipate comprising bis(2-ethylhexyl)adipate (DEHA), dimethyl adipate (DMAD), monomethyl adipate (MMAD), dioctyl adipate (DOA), Bis[2-(2-butoxyethoxy)ethyl] adipate, dibutyl adipate, diisobutyl adipate, diisodecyl adipate, a derivative thereof, or a combination thereof. In some embodiments, the plasticizer comprises a sebacate comprising dibutyl sebacate (DBS), Bis (2-ethylhexyl) sebacate, diethyl sebacate, dimethyl sebacate, a derivative thereof, or a combination thereof. In some embodiments, the plasticizer comprises a maleate comprising Bis(2-ethylhexyl) maleate, dibutyl maleate, diisobutyl maleate, a derivative thereof, or a combination thereof. In some embodiments, the plasticizer comprises a bio-based plasticizer comprising an acetylated monoglyceride, an alkyl citrate, a methyl ricinoleate, or a green plasticizer. In some embodiments, the alkyl citrate is selected from the group consisting of triethyl citrate, acetyl triethyl citrate, tributyl citrate, acetyl tributyl citrate, trioctyl citrate, acetyl trioctyl citrate, trihexyl citrate, acetyl trihexyl citrate, butyryl trihexyl citrate, trimethyl citrate, a derivative thereof, or a combination thereof. In some embodiments, the green plasticizer is selected from the group consisting of epoxidized soybean oil, epoxidized vegetable oil, epoxidized esters of soybean oil, a derivative thereof, or a combination thereof.

In some embodiments, the plasticizer comprises an azelate, a benzoate (e.g., sucrose benzoate), a terephthalate (e.g., dioctyl terephthalate), 1,2-cyclohexane dicarboxylic acid diisononyl ester, alkyl sulphonic acid phenyl ester, a sulfonamide (e.g., N-ethyl toluene sulfonamide, N-(2-hydroxypropyl) benzene sulfonamide, N-(n-butyl) benzene sulfonamaide), an organophosphate (e.g., tricresyl phosphate or tributyl phosphate), a glycol (e.g., triethylene glycol dihexanoate or tetraethylene glycol diheptanoate), a polyether, a polymeric plasticizer, polybutene, a derivative thereof, or a combination thereof.

In some embodiments, the photo-curable resin comprises a solvent. In some embodiments, the solvent comprises a nonpolar solvent. In certain embodiments, the nonpolar solvent comprises pentane, cyclopentane, hexane, cyclohexane, benzene, toluene, 1,4-dioxane, chloroform, diethyl ether, dichloromethane, a derivative thereof, or a combination thereof. In some embodiments, the solvent comprises a polar aprotic solvent. In certain embodiments, the polar aprotic solvent comprises tetrahydrofuran, ethyl acetate, acetone, dimethylformamide, acetonitrile, DMSO, propylene carbonate, a derivative thereof, or a combination thereof. In some embodiments, the solvent comprises a polar protic solvent. In certain embodiments, the polar protic solvent comprises formic acid, n-butanol, isopropyl alcohol, n-propanol, t-butanol, ethanol, methanol, acetic acid, water, a derivative thereof, or a combination thereof. In preferred embodiments, the photo-curable resin comprises less than 90% of the solvent by weight.

In some embodiments, the photo-curable resin comprises a biologically significant chemical. In some embodiments, the biologically significant chemical comprises a hormone, an enzyme, an active pharmaceutical ingredient, an antibody, a protein, a drug, or any combination thereof. In some embodiments, the biologically significant chemical comprises a pharmaceutical composition, a chemical, a gene, a polypeptide, an enzyme, a biomarker, a dye, a compliance indicator, an antibiotic, an analgesic, a medical grade drug, a chemical agent, a bioactive agent, an antibacterial, an antibiotic, an anti-inflammatory agent, an immune-suppressive agent, an immune-stimulatory agent, a dentinal desensitizer, an odor masking agent, an immune reagent, an anesthetic, a nutritional agent, an antioxidant, a lipopolysaccharide complexing agent or a peroxide.

In some embodiments, the added component (e.g., a polymerization catalyst, a polymerization inhibitor, a light blocker, a plasticizer, a solvent, a surface energy modifier, a pigment, a dye, a filler, or a biologically significant chemical) is functionalized so that it can be incorporated into the polymer network so that it cannot readily be extracted from the final cured material. In certain embodiments, the polymerization catalyst, polymerization inhibitor, light blocker, plasticizer, surface energy modifier, pigment, dye, and/or filler, are functionalized to facilitate their incorporation into the cured polymeric material. A polymer network, as used herein, can refer to a polymer composition comprising a plurality of polymer chains wherein a large portion (e.g., >80%) and optionally all the polymer chains are interconnected, for example via covalent crosslinking, to form a single polymer composition. In an embodiment, there is provided a radiopaque polymer in the form of a crosslinked network in which at least some of the crosslinks of the network structure are formed by covalent bonds.

Polymeric Materials

In some embodiments, the present disclosure provides polymeric materials formed from the photo-curable resins disclosed herein. In preferred embodiments, the polymeric material is formed from the photo-curable resins disclosed herein with additive manufacturing. In some embodiments, the polymeric material is prepared by a process comprising: providing the photo-curable resin as described herein; and forming the polymeric material from the photo-curable resin with additive manufacturing. In some preferred embodiments, the polymeric material is prepared by a process comprising: providing a photo-curable resin comprising: an oligomer having a number-average molecular weight of greater than 3,000 Da; and an initiator, wherein the photo-curable resin comprises less than 20 wt % hydrogen bonding units and has a viscosity less than or equal to 15,000 cP at 25° C.; and forming the polymeric material from the photo-curable resin with additive manufacturing. In certain preferred embodiments, the polymeric material is prepared by a process comprising: providing a photo-curable resin comprising: an oligomer having a number-average molecular weight of greater than 3,000 Da; and a photoinitiator, wherein the photo-curable resin comprises less than 10 wt % hydrogen bonding units; and forming the polymeric material from the photo-curable resin with additive manufacturing.

In some embodiments, the present disclosure provides a polymeric material having less than 10 wt % hydrogen bonding units, wherein the polymeric material is characterized by one or more of: a tensile modulus greater than or equal to 200 MPa after 24 hours in a wet environment at 37° C.; a flexural stress of greater than or equal to 1.5 MPa remaining after 24 hours in a wet environment at 37° C.; a hardness from 60 Shore A to 85 Shore D after 24 hours in a wet environment at 37° C.; an elongation at break greater than or equal to 15% before 24 hours in a wet environment at 37° C.; and an elongation at break greater than or equal to 15% after 24 hours in a wet environment at 37° C. In preferred embodiments, the polymeric material is formed from the photo-curable resins disclosed herein. Young's modulus is calculated with an algorithm that breaks the relevant portion of a stress strain curve into 6 regions with 0% overlap and applies a least square fitting to determine the slope. The pair of consecutive regions that have the highest slope sum are determined. From this pair, the modulus is assigned to region with the highest slope.

Property values of the polymeric material can be determined, for example, by using the following methods:
stress relaxation properties can be assessed using an RSA-G2 instrument from TA Instruments, with a 3-point bending, according to ASTM D790; stress relaxation can be measured at 30° C. and submerged in water, and reported as either the remaining load after 24 hours, and/or as the percent (%) of initial load;
storage modulus can be measured at 37° C. and is reported in MPa;
$T_g$ of the cured polymeric material can be assessed using dynamic mechanical analysis (DMA) and is provided herein as the tan δ peak when run at 1 hz with a temperature ramp of 2° C. a minute;
tensile modulus, tensile strength, elongation at yield and elongation at break can be assessed according to ISO 527-2 5B;
tensile strength at yield, elongation at break, tensile strength, and Young's modulus can be assessed according to ASTM D1708 or ASTM D638; and
flexural stress remaining after 24 hours in wet environment at 37° C. ("flexural stress remaining") can be assessed according to ASTM E328.

In embodiments, the polymeric material is characterized by a tensile stress-strain curve that displays a yield point after which the test specimen continues to elongate, but there is no increase in load. Such yield point behavior typically occurs "near" the glass transition temperature, where the material is between the glassy and rubbery regimes and may be characterized as having viscoelastic behavior. In embodiments, viscoelastic behavior is observed in the temperature range 20° C. to 40° C. The yield stress is determined at the yield point. In some embodiments, the yield point follows an elastic region in which the slope of the stress-strain curve is constant or nearly constant. In embodiments, the modulus is determined from the initial slope of the stress-strain curve or as the secant modulus at 1% strain (e.g. when there is no linear portion of the stress-strain curve). The elongation at yield is determined from the strain at the yield point. When the yield point occurs at a maximum in the stress, the ultimate tensile strength is less than the yield strength. For a tensile test specimen, the strain is defined by ln (l/l0), which may be approximated by (l–l0)/l0 at small strains (e.g. less than approximately 10%) and the elongation is l/l0, where l is the gauge length after some deformation has occurred and l0 is the initial gauge length. The mechanical properties can depend on the temperature at which they are measured. The test temperature may be below the expected use temperature for a dental appliance such as 35° C. to 40° C. In some embodiments, the test temperature is 23±2° C.

Properties of the polymeric material can be determined after a soak time in a wet environment. Determination of values after a soak time in a wet environment can be conducted on a 1-mm thick sample. For example, material properties of a polymeric material disclosed herein can be determined by obtaining a 1-mm thick sample of said polymeric material, and soaking in a wet environment for 24 hours at 37° C. (i.e., the material after 24 hours in a wet environment at 37° C.).

In some embodiments, the polymeric material has an elongation at break greater than 5%, greater than 10%, greater than 15%, greater than 20%, greater than 25%, greater than 30%, greater than 35%, greater than 40%, greater than 45%, or greater than 50% after 24 hours in a wet environment at 37° C. In some embodiments, the polymeric material has an elongation at break greater than 5%, greater than 10%, greater than 15%, greater than 20%, greater than 25%, greater than 30%, greater than 35%, greater than 40%, greater than 45%, or greater than 50% before 24 hours in a wet environment at 37° C. In preferred embodiments, the polymeric material has an elongation at break greater than 15% before and after 24 hours in a wet environment at 37° C.

In some embodiments, the polymeric material has a tensile strength at yield from 1 MPa to 100 MPa, from 5 MPa to 85 MPa, from 10 MPa to 75 MPa, from 15 Pa to 65 MPa, from 20 Pa to 55 MPa, or from 25 MPa to 45 MPa after 24 hours in a wet environment at 37° C. In preferred embodiments, the polymeric material has a tensile strength at yield from 10 MPa to 55 MPa after 24 hours in a wet environment at 37° C. In some embodiments, the polymeric material is characterized by a tensile strength at yield greater than or equal to 0.1 MPa, greater than or equal to 0.5 MPa, greater than or equal to 1 MPa, greater than or equal to 2 MPa, greater than or equal to 3 MPa, greater than or equal to 4 MPa, greater than or equal to 5 MPa, greater than or equal to 6 MPa, greater than or equal to 7 MPa, greater than or equal to 8 MPa, greater than or equal to 9 MPa, or greater than or equal to 10 MPa after 24 hours in a wet environment at 37° C. In preferred embodiments, the polymeric material is characterized by a tensile strength at yield greater than or equal 5 MPa after 24 hours in a wet environment at 37° C.

In some embodiments, the polymeric material has an ultimate tensile strength from 10 MPa to 100 MPa, from 15 MPa to 80 MPa, from 20 MPa to 60 MPa, from 25 MPa to 50 MPa, from 25 MPa to 45 MPa, from 25 MPa to 40 MPa, from 30 MPa to 45 MPa, or from 30 MPa to 40 MPa after 24 hours in a wet environment at 37° C. In preferred embodiments, the polymeric material has an ultimate tensile strength from 10 MPa to 50 MPa after 24 hours in a wet environment at 37° C.

In some embodiments, the polymeric material has a tensile modulus from 100 MPa to 3000 MPa, from 200 MPa to 3000 MPa, from 250 MPa to 2750 MPa, from 400 MPa to 2500 MPa, from 600 MPa to 2250 MPa, or from 800 MPa to 2000 MPa after 24 hours in a wet environment at 37° C. In some embodiments, the polymeric material has a tensile modulus of greater or equal to 100 MPa, greater or equal to 200 MPa, greater or equal to 300 MPa, greater or equal to 400 MPa, greater or equal to 500 MPa, greater or equal to 600 MPa, greater or equal to 700 MPa, greater or equal to 800 MPa, greater or equal to 900 MPa, greater or equal to 1000 MPa, greater or equal to 1100 MPa, greater or equal to 1200 MPa, greater or equal to 1300 MPa, greater or equal to 1400 MPa, or greater or equal to 1500 MPa after 24 hours in a wet environment at 37° C. In some preferred embodiments, the polymeric material has a tensile modulus of greater than 200 MPa after 24 hours in a wet environment at 37° C. In some preferred embodiments, the polymeric material has a tensile modulus from 1.0 GPa to 1.4 GPa after 24 hours in a wet environment at 37° C. In some preferred embodiments, the polymeric material is characterized by a tensile modulus greater than or equal to 200 MPa after 24 hours in a wet environment at 37° C.

In some embodiments, the polymeric material has a flexural stress relaxation remaining ("flexural stress remaining") greater than or equal to 5%, greater than or equal to 10%, greater than or equal to 15%, greater than or equal to 20%, greater than or equal to 35%, greater than or equal to 40%, greater than or equal to 45%, greater than or equal to 50%, greater than or equal to 55%, or greater than or equal to 60% after 24 hours in a wet environment at 37° C. In some preferred embodiments the polymeric material has a flexural stress remaining of greater than or equal to 10% after 24 hours in a wet environment at 37° C. In some embodiments, the polymeric material is characterized by a flexural stress remaining from 5% to 45%, from 10% to 45%, from 15% to 45%, from 20% to 45%, from 25% to 45%, or from 30% to 45% of the initial load after 24 hours in a wet environment at 37° C. In some preferred embodiments, the polymeric material is characterized by a flexural stress remaining from 20% to 45% of the initial load after 24 hours in a wet environment at 37° C.

In some embodiments, the polymeric material is characterized by a flexural stress remaining from 0.01 MPa to 15 MPa, from 0.05 MPa to 15 MPa, from 0.1 MPa to 15 MPa, from 0.5 MPa to 15 MPa, from 1 MPa to 15 MPa, from 2 MPa to 15 MPa, from 3 MPa to 15 MPa, from 4 MPa to 15 MPa, from 5 MPa to 15 MPa, or from 10 MPa to 15 MPa after 24 hours in a wet environment at 37° C. In some preferred embodiments, the polymeric material is characterized by a flexural stress remaining from 2 MPa to 15 MPa after 24 hours in a wet environment at 37° C. In some embodiments, the polymeric material is characterized by a flexural stress of greater than or equal to 0.1 MPa, greater than or equal to 0.5 MPa, greater than or equal to 1 MPa, greater than or equal to 1.5 MPa, greater than or equal to 2 MPa, greater than or equal to 2.5 MPa, greater than or equal to 3 MPa, greater than or equal to 4 MPa, greater than or equal to 5 MPa, greater than or equal to 6 MPa, greater than or equal to 7 MPa, greater than or equal to 8 MPa, greater than or equal to 9 MPa, greater than or equal to 10 MPa, or greater than or equal to 15 MPa remaining after 24 hours in a wet environment at 37° C. In some preferred embodiments, the polymeric material is characterized by a flexural stress of greater than or equal to 1.5 MPa remaining after 24 hours in a wet environment at 37° C.

In certain embodiments, it is advantageous that the polymeric material have a high flexural stress remaining, forming relatively stiff materials. In some applications relating to use of hard materials (e.g., aeronautical engineering, medical implants), a polymeric material formed from the photocurable resins disclosed herein would be advantageous due to the availability of conventional 3D printers to form these polymeric materials having the desired characteristics. In some embodiments, the polymeric material has a flexural modulus remaining of 50 MPa or more, 60 MPa or more, 70 Pa or more, 80 Pa or more, 90 Pa or more, 100 Pa or more, 125 Pa or more, or 150 MPa or more after 24 hours in a wet environment at 37° C.

In certain other embodiments, it is advantageous that the polymeric material have a relatively low flexural stress remaining, forming materials that are not overly-stiff. In some embodiments, the polymeric material has a flexural modulus remaining of 80 MPa or less, 70 MPa or less, 60 MPa or less, 55 MPa or less, 50 MPa or less, or 45 MPa or less after 24 hours in a wet environment at 37° C.

In some embodiments, a polymeric material will have a flexural stress remaining after a period of time of use. As a non-limiting example, an orthodontic appliance (e.g., an aligner) can be formed of a polymeric material having a high flexural stress. In some embodiments, following application of the appliance to the teeth of a patient, there can be a significant and fast decrease of flexural stress (e.g., over the course of minutes). Such decreases in flexural stress can follow an exponential curve of decrease leading towards an asymptote during the intended lifetime of the appliance (e.g., over the course of weeks for an orthodontic appliance such as an aligner). Orthodontic appliances may have an initial period of discomfort that, following a period of use, decreases corresponding with a decrease of flexural stress remaining. In some embodiments, the polymeric material has a flexural stress remaining of 90 MPa or less, 85 MPa or less, 80 MPa or less, 75 MPa or less, 70 MPa or less, 65 MPa or less, 60 MPa or less, 55 MPa or less, or 50 MPa or less after a time period of use. In preferred embodiments, the polymeric material has a flexural stress remaining of 80 MPa or less after a time period of use. In some embodiments, the time period of use is 1 minute, 5 minutes, 10 minutes, 30 minutes, 1 hour, or 24 hours. As a non-limiting example, an aligner composed of polymeric material placed onto a patient's teeth that is removed after 10 minutes and has a flexural stress of 70 MPa would have a polymeric material characterized by a flexural stress remaining of 70 MPa after a time period of use, wherein said time period is 10 minutes.

In certain embodiments, the polymeric material is characterized by an elongation at yield of greater than or equal to 1%, greater than or equal to 2%, greater than or equal to 3%, greater than or equal to 4%, greater than or equal to 5%, greater than or equal to 6%, greater than or equal to 7%, greater than or equal to 8%, greater than or equal to 9%, greater than or equal to 10%, greater than or equal to 15%, or greater than or equal to 20% after 24 hours in a wet environment at 37° C. (i.e., following exposure to a wet environment for 24 hours). In some embodiments, the polymeric material is characterized by an elongation at yield of greater than or equal to 1%, greater than or equal to 2%, greater than or equal to 3%, greater than or equal to 4%, greater than or equal to 5%, greater than or equal to 6%, greater than or equal to 7%, greater than or equal to 8%, greater than or equal to 9%, greater than or equal to 10%, greater than or equal to 15%, or greater than or equal to 20% before 24 hours in a wet environment at 37° C. In preferred embodiments, the polymeric material is characterized by an elongation at yield of greater than or equal to 4% before and after 24 hours in a wet environment at 37° C.

In some embodiments, the polymeric material has a maximum force at 5% strain greater than or equal to 3 pound-force per 3.57 $cm^2$. As a non-limiting example, the sample is a rectangular slab having a width of 2.1 cm and a distance between support of 1.7 cm. In some embodiments, the polymeric material has a remaining force greater than 0.1 pound-force per 3.57 $cm^2$ after being submerged for 24 hours in a wet environment having a temperature of 37° C.

In some embodiments, the polymeric material is characterized by an elongation at yield from 1% to 10%, from 2% to 10%, from 3% to 10%, from 4% to 10%, from 5% to 10%, from 1% to 15%, from 1% to 20%, or from 1% to 25% after 24 hours in a wet environment at 37° C. In some embodiments, the polymeric material is characterized by an elongation at yield from 1% to 10%, from 2% to 10%, from 3% to 10%, from 4% to 10%, from 5% to 10%, from 1% to 15%, from 1% to 20%, or from 1% to 25% before 24 hours in a wet environment at 37° C. In preferred embodiments, the polymeric material is characterized by an elongation at yield from 4% to 10% before and after 24 hours in a wet environment at 37° C.

In some embodiments, the polymeric material is characterized by an elongation at break of greater than 5%, greater than 10%, greater than 15%, greater than 20%, greater than 25%, greater than 30%, greater than 35%, greater than 40%, greater than 45%, or greater than 50% after 24 hours in a wet environment at 37° C. In some embodiments, the polymeric material is characterized by an elongation at break of greater than 5%, greater than 10%, greater than 15%, greater than 20%, greater than 25%, greater than 30%, greater than 35%, greater than 40%, greater than 45%, or greater than 50% before 24 hours in a wet environment at 37° C. In preferred embodiments, the polymeric material is characterized by an elongation at break of greater than 15% before and after 24 hours in a wet environment at 37° C. In some embodiments, the polymeric material is characterized by an elongation at break from 5% to 250%, from 10% to 250%, from 15% to 250%, from 20% to 250%, from 25% to 250%, from 30% to 250%, from 35% to 250%, from 40% to 250%, from 45% to 250%, from 50% to 250%, from 75% to 250%, or from 100% to 250% after 24 hours in a wet environment at 37° C. In some embodiments, the polymeric material is characterized by an elongation at break from 5% to 250%, from 10% to 250%, from 15% to 250%, from 20% to 250%, from 25% to 250%, from 30% to 250%, from 35% to 250%, from 40% to 250%, from 45% to 250%, from 50% to 250%, from 75% to 250%, or from 100% to 250% before 24 hours in a wet environment at 37° C. In preferred embodiments, the polymeric material is characterized by an elongation at break from 40% to 250% before and after 24 hours in a wet environment at 37° C.

In some embodiments, the polymeric material is characterized by a storage modulus from 0.1 MPa to 4000 MPa, from 50 MPa to 2750 MPa, from 100 MPa to 2500 MPa, from 200 MPa to 2250 MPa, from 300 MPa to 3000 MPa, from 500 MPa to 3000 MPa, from 750 MPa to 3000 MPa, or from 1000 MPa to 3000 MPa after 24 hours in a wet environment at 37° C. In preferred embodiments, the polymeric material is characterized by a storage modulus from 750 MPa to 3000 MPa after 24 hours in a wet environment at 37° C.

In some embodiments, the polymeric material has at least one glass transition temperature ($T_g$) from 0° C. to 150° C. In preferred embodiments, the polymeric material has at least one glass transition temperature greater than 60° C. In even more preferred embodiments, the polymeric material has at least one glass transition temperature greater than 75° C. In some embodiments, the at least one glass transition temperature is from 0° C. to 200° C., from 0° C. to 140° C., from 0° C. to 20° C., from 20° C. to 40° C., from 40° C. to 60° C., from 60° C. to 80° C., from 80° C. to 100° C., from 100° C. to 120° C., from 120° C. to 140° C., from 140° C. to 160° C., from 160° C. to 180° C., from 180° C. to 200° C., from 0° C. to 35° C., from 35° C. to 65° C., from 65° C. to 100° C., from 0° C. to 50° C., or from 50° C. to 100° C. In some embodiments, the polymeric material has at least one glass transition temperature from 0° C. to 10° C., from 10° C. to 20° C., from 20° C. to 30° C., from 30° C. to 40° C., from 40° C. to 50° C., from 50° C. to 60° C., from 60° C. to 70° C., from 70° C. to 80° C., or from 80° C. to 90° C. In some embodiments, the polymeric material has at least one glass transition temperature from −100° C. to 40° C., from −80° C. to 10° C., from −70° C. to 0° C., from −70° C. to −10° C., from −70° C. to −20° C., from −70° C. to −30° C., from −70° C. to −40° C., from −70° C. to −50° C., or from −80° C. to −40° C. In some embodiments, the polymeric material has at least two glass transition temperatures. In certain embodiments, the polymeric material has a first glass transition temperature less than or equal to 40° C. and a second glass transition temperature greater than or equal to 60° C. In some embodiments, the polymeric material has a first glass transition temperature less than or equal to 0° C. and a second glass transition temperature greater than or equal to 60° C. In some embodiments, the polymeric material has a first glass transition temperature less than or equal to 0° C. and a second glass transition temperature greater than or equal to 75° C. In some embodiments, the polymeric material has a first glass transition temperature less than −20° C. and a second glass transition temperature greater than 80° C.

In some embodiments, the polymeric material comprises an aliphatic urethane (meth)acrylate. In some embodiments, the polymeric material comprises isobornyl (meth)acrylate, trimethylolpropane tri(meth)acrylate, 3,3,5-trimethcyclohexyl 2-((meth)acryloxy) benzoate, 3,3,5-Trimethylcyclohexyl (meth)acrylate, tripropylene glycol di(meth)acrylate, hexane-1,6-diol di(meth)acrylate, hydroxyethyl (meth)acrylate, benzyl (meth)acrylate, a derivative thereof, or a combination thereof. In some embodiments, the polymeric material comprises Dymax BRC-4421, Exothane 108, Exothane 10, isophorone urethane di(meth)acrylate (e.g., IPDI-UDMA), CN991, CN9782, CN3211, CN9782, CN9009, PU3201NT or a combination thereof.

Low levels of water absorption are favorable for polymeric materials described herein. Water absorption can occur when a polymeric material is exposed to a wet environment (e.g., a patient's mouth using an orthodontic appliance formed from a polymeric material). Properties of the polymeric material can degrade when water absorption reaches a threshold value, typically greater than 22 wt %. It is preferred herein that the polymeric materials have low levels of water uptake. In some embodiments, the polymeric material formed from the photo-curable resin comprises a water uptake of less than 25 wt %, less than 20 wt %, less than 15 wt %, less than 10 wt %, less than 5 wt %, less than 4 wt %, less than 3 wt %, less than 2 wt %, less than 1 wt %, less than 0.5 wt %, less than 0.25 wt %, or less than 0.1 wt %. In preferred embodiments, the polymeric material formed from the photo-curable resin comprises a water uptake of less than 2 wt %. In more preferred embodiments, the polymeric material formed from the photo-curable resin comprises a water uptake of less than 1 wt %. In even more preferred embodiments, the polymeric material formed from the photo-curable resin comprises a water uptake of less than 0.5 wt %. In embodiments described herein, the water uptake is measured after 24 hours in a wet environment at 37° C. In some embodiments, a polymer formed from the oligomer of the resin is hydrophobic. In preferred embodiments, the polymeric material formed from the photo-curable resin is hydrophobic.

In some embodiments, the polymeric material is characterized by having a low water uptake. In some embodiments, the polymeric material comprises less than 40 wt %, less than 35 wt %, less than 30 wt %, less than 25 wt %, less than 20 wt %, less than 15 wt %, less than 10 wt %, less than 5 wt %, less than 4 wt %, less than 3 wt %, less than 2 wt %, or less than 1 wt % water after 24 hours in a wet environment at 37° C. In preferred embodiments, the polymeric material comprises less than 2 wt % water after 24 hours in a wet environment at 37° C. In more preferred embodiments, the polymeric material comprises less than 1 wt % water after 24 hours in a wet environment at 37° C. In even more preferred embodiments, the polymeric material comprises less than 0.5 wt % water after 24 hours in a wet environment at 37° C.

The polymeric materials formed from the photo-curable resin can have high conversion rates, or high extent of reactions. In some embodiments, the polymeric material comprises 20-100 wt % of the polymer formed from the oligomer(s) and/or monomer(s) of the photo-curable resin. In some embodiments, the polymeric material comprises greater than 20 wt %, greater than 30 wt %, greater than 40 wt %, greater than 50 wt %, greater than 60 wt %, greater than 70 wt %, greater than 80 wt %, greater than 85 wt %, greater than 90 wt %, greater than 95 wt %, greater than 98 wt %, or greater than 99 wt % of the polymer formed from the oligomer(s) and/or monomer(s) of the photo-curable resin. In certain embodiments, it is preferable to have a high conversion percentage of oligomer(s) and/or monomer(s) into polymer when forming the polymeric material. In some embodiments, the formed polymer is hydrophobic.

In some embodiments, the polymeric materials formed from the photo-curable resin have high conversion rates of reactive group double bonds (e.g., acrylates or methacrylates) to single bonds, indicating incorporation into the polymeric material. In some embodiments, the conversion of reactive double bonds in the resin to single bonds in the polymeric material can be measured by FTIR (e.g., by measuring relative amounts before and after curing). In some embodiments, the polymeric material formed from the photo-curable resin has greater than 60%, greater than 70%, greater than 80%, greater than 90%, or greater than 95% conversion of double bonds to single bonds.

In some embodiments, the polymeric materials formed from the photo-curable resin have low levels of extractable materials (e.g., unreacted monomers from said photo-curable resin). The amount of extractable materials can be determined by weight loss of the polymeric material after soaking in water for 1 week, after soaking in ethanol for 48 hours, or after soaking in hexane for 48 hours. A general experiment for determining the amount of extractable material includes the steps of (i) weighing a dried sample of the polymeric material; (ii) soaking the sample in a solvent at a given temperature (e.g., 25° C.) for a period of time; (iii) refreshing the solvent until extraction is completed; (iv) drying the sample in an oven; (v) weighing the extracted sample; and (vi) calculating the weight loss. In some embodiments, the polymeric materials formed from the photo-curable resin have less than 5 wt %, less than 4 wt %, less than 3 wt %, less than 2 wt %, less than 1 wt %, less than 0.75 wt %, less than 0.5 wt %, or less than 0.25 wt % extractable materials.

In some embodiments, the polymeric material has less than 20 wt %, less than 15 wt %, less than 10 wt %, less than 9 wt %, less than 8 wt %, less than 7 wt %, less than 6 wt %, less than 5 wt %, less than 4 wt %, less than 3 wt %, less than 2 wt %, or less than 1 wt % hydrogen bonding units, as calculated or measured by weight percentage of hydrogen bonding groups, further described herein. In preferred embodiments, the polymeric material has less than or equal to 10 wt % hydrogen bonding units.

In some embodiments, the polymeric material further comprises a thermal initiator, a second polymer, a crosslinking moiety, or a combination thereof.

In some embodiments, the polymeric material comprises the second polymer, and the wt % ratio of the polymer formed from the oligomer to the second polymer is from 100:1-1:100, from 50:1-1:50, from 40:1-1:40, from 30:1-1:30, from 25:1-1:25, from 20:1-1:20, from 15:1-1:15, from 10:1-1:10, from 5:1-1:5, from 4:1-1:4, from 3:1-1:3, from 2:1-1:2, 100:1 or less, 50:1 or less, 40:1 or less, 30:1 or less, 25:1 or less, 20:1 or less, 15:1 or less, 10:1 or less, 9:1 or less, 8:1 or less, 7:1 or less, 6:1 or less, 5:1 or less, 4:1 or less, 3:1 or less, 2:1 or less, or 1:1 or less.

In some embodiments, the polymeric material comprises 0-50 wt % of the crosslinking moiety. In some embodiments, the polymeric material comprises 30 wt % or less of the crosslinking moiety. In some embodiments, the polymeric material comprises from 0 to 0.5 wt % of the thermal initiator. In certain embodiments the thermal initiator comprises azobisisobutyronitrile, 2,2'-azodi(2-methylbutyronitrile), or a combination thereof.

In some embodiments, the polymeric material is clear, substantially clear, mostly clear, or opaque. In certain embodiments, the polymeric material is clear. In certain embodiments, the polymeric material is substantially clear. In certain embodiments, the polymeric material is mostly clear. In some embodiments, greater than 70% of visible light passes through the polymeric material. In certain embodiments, greater than 80% of visible light passes through the polymeric material. In certain embodiments, greater than 90% of visible light passes through the polymeric material. In certain embodiments, greater than 95% of visible light passes through the polymeric material. In certain embodiments, greater than 99% of visible light passes through the polymeric material. Transparency can be measured using a UV-Vis spectrophotometer. In some embodiments, the transparency is measured by measuring the passage of a wavelength of transparency. In some embodiments, greater than 70%, greater than 80%, greater than 90%, greater than 95%, or greater than 99% of the wavelength of transparency can pass through the polymeric material. In some embodiments, the wavelength of transparency is in the visible light range (i.e., from 400 nm to 800 nm), is in the infrared light range, or is in the ultraviolet light range. In some embodiments, the polymeric material does not have color. In other embodiments, the polymeric material appears white, off-white, or mostly transparent with white coloring, as detected by the human eye.

In some embodiments, greater than 20%, greater than 30%, greater than 40%, greater than 50%, greater than 60%, greater than 70%, greater than 80%, greater than 90%, or greater than 95% of visible light passes through the polymeric material after 24 hours in a wet environment at 37° C. In preferred embodiments, greater than 70% of visible light passes through the polymeric material after 24 hours in a wet environment at 37° C.

In some embodiments, the polymeric material is biocompatible, bioinert, or a combination thereof.

In some embodiments, the polymeric material is formed using 3D printing (i.e., by additive manufacturing) using photopolymerization. In certain embodiments, the polymeric material is formed using conventional 3D printers. In some embodiments, the polymeric material can be used in coatings, molds, injection molding machines, or other manufacturing methods that use or could use light during the curing process. In some embodiments, the polymeric material is well suited for applications that require, e.g., solvent resistance, humidity resistance, water resistance, creep resistance, or heat deflection resistance.

Methods of Making Polymeric Materials

In some embodiments, the present disclosure provides methods for making or otherwise fabricating the polymeric materials described herein, preferably wherein said polymeric materials are formed from the photo-curable resins disclosed herein. In some embodiments, present disclosure provides a method for making a polymeric material, the method comprising: providing a photo-curable resin as described herein; and producing a product, wherein producing the product comprises additive manufacturing.

In some embodiments, the present disclosure provides a method for forming a polymeric material, the method comprising:

providing a photo-curable resin disclosed herein; and
curing the photo-curable resin, forming the polymeric material disclosed herein. In some embodiments, curing the photo-curable resin comprises exposing the photo-curable resin to a light source. In some embodiments, the method further comprises the step of fabricating a device using an additive manufacturing device, wherein said additive manufacturing device facilitates the curing. In some embodiments, the curing of the photo-curable resin produces the polymeric material. In certain embodiments, the photo-curable resin is cured using an additive manufacturing device to produce the polymeric material. In some embodiments, the method further comprises the step of cleaning the polymeric material. In certain embodiments, the cleaning of the polymeric material includes washing and/or rinsing the polymeric material with a solvent, which can remove monomers and undesired impurities from the polymeric material.

In some embodiments, the photo-curable resins are curable and have melting points <90° C. in order to be liquid and, thus, processable at the temperatures usually employed in currently available additive manufacturing techniques. Said photo-curable resins comprise at least one photopolymerization initiator (i.e., a photoinitiator) and may be heated to a predefined elevated process temperature ranging from 40° C. to 150° C., such as from 90° C. to 120° C., before becoming irradiated with light of a suitable wavelength to be absorbed by said photoinitiator, thereby causing a cleavage of the photoinitiator to induce polymerization of the photo-curable resin to obtain an optionally crosslinked polymeric material.

In some embodiments, the methods disclosed herein are part of a high temperature lithogra-phy-based photopolymerization process, wherein a curable composition (i.e., the photo-curable resin) comprises at least one photopolymerization initiator and is heated, which makes high temperature lithography-based photopolymerization process more preferably is an additive manufacturing process, most preferably a 3D printing process. The method according to the present disclosure offers the possibility of quickly and facilely producing devices, such as orthodontic appliances, by additive manufacturing such as 3D printing using photo-curable resins as disclosed herein.

Photopolymerization occurs when suitable formulations (e.g., the photo-curable resins disclosed herein) are exposed to radiation (e.g., UV or visible light) of sufficient power and of a wavelength capable of initiating polymerization. The wavelengths and/or power of radiation useful to initiate polymerization may depend on the photoinitiator used. "Light" as used herein includes any wavelength and power capable of initiating polymerization. Some wavelengths of light include ultraviolet (UV) or visible. UV light sources include UVA (wavelength about 400 nanometers (nm) to about 320 nm), UVB (about 320 nm to about 290 nm) or UVC (about 290 nm to about 100 nm). Any suitable source may be used, including laser sources. The source may be broadband or narrowband, or a combination thereof. The light source may provide continuous or pulsed light during the process. Both the length of time the system is exposed to UV light and the intensity of the UV light can be varied to determine the ideal reaction conditions.

In some embodiments, the methods disclosed herein use additive manufacturing to produce a device comprising the polymeric material. In certain embodiments, the methods disclosed herein use additive manufacturing to produce a device consisting essentially of the polymeric material. Additive manufacturing includes a variety of technologies which fabricate three-dimensional objects directly from digital models through an additive process. In some aspects, successive layers of material are deposited and "cured in place". A variety of techniques are known to the art for additive manufacturing, including selective laser sintering (SLS), fused deposition modeling (FDM) and jetting or extrusion. In many embodiments, selective laser sintering involves using a laser beam to selectively melt and fuse a layer of powdered material according to a desired cross-sectional shape in order to build up the object geometry. In many embodiments, fused deposition modeling involves melting and selectively depositing a thin filament of thermoplastic polymer in a layer-by-layer manner in order to form an object. In yet another example, 3D printing can be used to fabricate the appliances herein. In many embodiments, 3D printing involves jetting or extruding one or more materials (e.g., the photo-curable resins disclosed herein) onto a build surface in order to form successive layers of the object geometry. In some embodiments, the resins described herein can be used in inkjet or coating applications. Polymeric materials may also be fabricated by "vat" processes in which light is used to selectively cure a vat or reservoir of the curable resin (e.g., the resins disclosed herein). Each layer of photo-curable resin may be selectively exposed to light in a single exposure or by scanning a beam of light across the layer. Specific techniques include sterolithography (SLA), Digital Light Processing (DLP) and two photon-induced photopolymerization (TPIP).

In some embodiments, the methods disclosed herein use continuous direct fabrication to produce a device comprising the polymeric material. In certain embodiments, the methods disclosed herein use continuous direct fabrication to produce a device consisting essentially of the polymeric material. A non-limiting exemplary direct fabrication process can achieve continuous build-up of an object geometry by continuous movement of a build platform (e.g., along the vertical or Z-direction) during an irradiation phase, such that the hardening depth of the irradiated photopolymer (e.g., the irradiated resin, hardening during the formation of the polymeric material) is controlled by the movement speed. Accordingly, continuous polymerization of material (e.g., polymerization of the resin into the polymeric material) on the build surface can be achieved. Such methods are described in U.S. Pat. No. 7,892,474, the disclosure of which is incorporated herein by reference in its entirety. In yet another example, a continuous direct fabrication method utilizes a "heliolithography" approach in which the liquid resin (e.g., the polymeric material) is cured with focused radiation while the build platform is continuously rotated and raised. Accordingly, the object geometry can be continuously built up along a spiral build path. Such methods are described in U.S. Patent Publication No. 2014/0265034, the disclosure of which is incorporated herein by reference in its entirety. Continuous liquid interface production of 3D objects has also been reported (J. Tumbleston et al., Science, 2015, 347 (6228), pp 1349-1352) hereby incorporated by reference in its entirety for description of the process. Another example of continuous direct fabrication method can involve extruding a material composed of a polymeric material surrounding a solid strand. The material can be extruded along a continuous three-dimensional path in order to form the object. Such methods are described in U.S. Patent Publication No. 2014/0061974, the disclosure of which is incorporated herein by reference in its entirety.

In some embodiments, the methods disclosed herein use high temperature lithography to produce a device comprising the polymeric material. In certain embodiments, the methods disclosed herein use high temperature lithography to produce a device consisting essentially of the polymeric material. "High temperature lithography," as used herein, may refer to any lithography-based photopolymerization processes that involve heating photopolymerizable material(s) (e.g., curable resins disclosed herein). The heating may lower the viscosity of the photopolymerizable material(s) before and/or during curing. Non-limiting examples of high-temperature lithography processes include those processes described in WO 2015/075094, WO 2016/078838 and WO 2018/032022. In some implementations, high-temperature lithography may involve applying heat to material to temperatures between 50° C.-120° C., such as 90° C.-120° C., 100° C.-120° C., 105° C.-115° C., 108° C.-110° C., etc. The material may be heated to temperatures greater than 120° C. It is noted other ranges may be used without departing from the scope and substance of the inventive concepts described herein.

In another embodiment, the methods disclosed herein comprise a continuous direct fabrication step. The continuous direct fabrication step can involve extruding a material composed of a curable liquid material (e.g., the photo-curable resin) surrounding a solid strand. The liquid material can be extruded along a continuous three-dimensional path in order to form an object or device. Such methods are described in U.S. Patent Publication No. 2014/0061974, the disclosure of which is incorporated herein by reference in its entirety.

In some preferred embodiments, the methods disclosed herein further comprise exposing the photo-curable resin to a light source. In some preferred embodiments, the methods disclosed herein further comprise heating the polymeric material to an elevated temperature. In certain embodiments, the elevated temperature is from 40° C. to 150° C. In some embodiments, heating the polymeric material to the elevated temperature occurs after curing the photo-curable resin. In certain embodiments, a thermal cure occurs by heating the polymeric material comprising a thermal initiator to an elevated temperature following the photo-curing step.

In some preferred embodiments, the methods disclosed herein further comprises fabricating an object with the polymeric material. In certain embodiments, fabricating the object comprises additive manufacturing. In some embodiments, fabricating the object with the polymeric material comprises printing with a 3D printer. In some embodiments, fabricating the object with the polymeric material comprises digital light projection. In certain embodiments, fabricating the object with the polymeric material comprises using hot lithography.

In some embodiments, the object is an orthodontic appliance. In some embodiments, the orthodontic appliance is an aligner, expander or spacer. In some embodiments, the orthodontic appliance comprises a plurality of tooth receiving cavities configured to reposition teeth from a first configuration toward a second configuration. In some embodiments, the orthodontic appliance is one of a plurality of orthodontic appliances configured to reposition the teeth from an initial configuration toward a target configuration. In some embodiments, the orthodontic appliance is one of a plurality of orthodontic appliances configured to reposition the teeth from an initial configuration toward a target configuration according to a treatment plan.

Devices Using Polymeric Materials

In some embodiments, the present disclosure provides devices comprising the polymeric materials generated from the photo-curable resins as described further herein. In some embodiments, the polymeric material is used to create a device intended to be placed in the intraoral cavity of a human. Such devices can be, for example, aligners that help to move teeth to new positions. In some embodiments, the devices can be retainers that help to keep teeth from moving to a new position. In some embodiments, the device can be used to expand the palate, move the location of the jaw, or prevent snoring of a human.

In some embodiments, the present disclosure provides methods for producing the devices described herein, said devices comprising a polymeric material. In some embodiments, the method comprises a step of shaping a photo-curable resin into a desirable shape prior to a step of curing the photo-curable resin, thereby generating the polymeric material having said desirable shape. In some embodiments, the method comprises a step of shaping a photo-curable into a desirable shape during a step of curing the photo-curable, thereby generating the polymeric material having said desirable shape. In some embodiments, the method comprises a step of curing the photo-curable resin, thereby forming the polymeric material, then shaping the polymeric material into a desirable shape. In some embodiments, the desirable shape is an orthodontic appliance. In some embodiments, the desirable shape is a device and/or object as disclosed herein. In some embodiments, the shaping step comprises extrusion, production of a sheet, production of a film, melt spinning, coating, injection molding, compression and transfer molding, blow molding, rotational blow molding, thermoforming, casting, or a combination thereof.

Exemplary embodiments of devices that can be cured using the materials disclosed herein include dental appliances for use in humans. In some embodiments, such devices can be used as treatment systems for providing an orthodontic treatment.

In certain aspects, the present disclosure provides a method of making an orthodontic appliance comprising a polymeric material, the method comprising providing a photo-curable resin as further described herein; and fabricating the polymer material by a direct or additive fabrication process. The photo-curable resin may be exposed to light in said direct or additive fabrication process. The process may further comprise an additional curing step following fabrication of the polymeric material.

In certain aspects, the present disclosure provides an orthodontic appliance comprising a polymeric material as further described herein. The orthodontic appliance may be an aligner, expander or spacer. In some embodiments, the orthodontic appliance comprises a plurality of tooth receiving cavities configured to reposition teeth from a first configuration toward a second configuration. In some embodiments, the orthodontic appliance is one of a plurality of orthodontic appliances configured to reposition the teeth from an initial configuration toward a target configuration, optionally according to a treatment plan. As used herein a "plurality of teeth" encompasses two or more teeth.

In many embodiments, one or more posterior teeth comprises one or more of a molar, a premolar or a canine, and one or more anterior teeth comprising one or more of a central incisor, a lateral incisor, a cuspid, a first bicuspid or a second bicuspid.

The curable resins and cured polymeric materials according to the present disclosure exhibit favorable thermomechanical properties for use as orthodontic appliances, for example, for moving one or more teeth.

The embodiments disclosed herein can be used to couple groups of one or more teeth to each other. The groups of one or more teeth may comprise a first group of one or more anterior teeth and a second group of one or more posterior teeth. The first group of teeth can be coupled to the second group of teeth with the polymeric shell appliances as disclosed herein.

The embodiments disclosed herein are well suited for moving one or more teeth of the first group of one or more teeth or moving one or more of the second group of one or more teeth, and combinations thereof.

The embodiments disclosed herein are well suited for combination with one or known commercially available tooth moving components such as attachments and polymeric shell appliances. In many embodiments, the appliance and one or more attachments are configured to move one or more teeth along a tooth movement vector comprising six degrees of freedom, in which three degrees of freedom are rotational and three degrees of freedom are translation.

The present disclosure provides orthodontic systems and related methods for designing and providing improved or more effective tooth moving systems for eliciting a desired tooth movement and/or repositioning teeth into a desired arrangement.

Although reference is made to an appliance comprising a polymeric shell appliance, the embodiments disclosed herein are well suited for use with many appliances that receive teeth, for example appliances without one or more of polymers or shells. The appliance can be fabricated with one or more of many materials such as metal, glass, reinforced fibers, carbon fiber, composites, reinforced composites, aluminum, biological materials, and combinations thereof for example. In some cases, the reinforced composites can comprise a polymer matrix reinforced with ceramic or metallic particles, for example. The appliance can be shaped in many ways, such as with thermoforming or direct fabrication as described herein, for example. Alternatively or in combination, the appliance can be fabricated with machining such as an appliance fabricated from a block of material with computer numeric control machining. Preferably, the appliance is fabricated using a curable resin according to the present disclosure.

Turning now to the drawings, in which like numbers designate like elements in the various figures, FIG. 1A illustrates an exemplary tooth repositioning appliance or aligner 100 that can be worn by a patient in order to achieve an incremental repositioning of individual teeth 102 in the jaw, and comprises the cured polymeric material disclosed herein. The appliance can include a shell (e.g., a continuous polymeric shell or a segmented shell) having teeth-receiving cavities that receive and resiliently reposition the teeth. An appliance or portion(s) thereof may be indirectly fabricated using a physical model of teeth. For example, an appliance (e.g., polymeric appliance) can be formed using a physical model of teeth and a sheet of suitable layers of polymeric material. In some embodiments, a physical appliance is directly fabricated, e.g., using rapid prototyping fabrication techniques, from a digital model of an appliance. An appliance can fit over all teeth present in an upper or lower jaw, or less than all of the teeth. The appliance can be designed specifically to accommodate the teeth of the patient (e.g., the topography of the tooth-receiving cavities matches the topography of the patient's teeth) and may be fabricated based on positive or negative models of the patient's teeth generated by impression, scanning, and the like. Alternatively, the appliance can be a generic appliance configured to receive the teeth, but not necessarily shaped to match the topography of the patient's teeth. In some cases, only certain teeth received by an appliance will be repositioned by the appliance while other teeth can provide a base or anchor region for holding the appliance in place as it applies force against the tooth or teeth targeted for repositioning. In some cases, some, most, or even all of the teeth will be repositioned at some point during treatment. Teeth that are moved can also serve as a base or anchor for holding the appliance as it is worn by the patient. Typically, no wires or other means will be provided for holding an appliance in place over the teeth. In some cases, however, it may be desirable or necessary to provide individual attachments or other anchoring elements 104 on teeth 102 with corresponding receptacles or apertures 106 in the appliance 100 so that the appliance can apply a selected force on the tooth. Exemplary appliances, including those utilized in the Invisalign® System, are described in numerous patents and patent applications assigned to Align Technology, Inc. including, for example, in U.S. Pat. Nos. 6,450,807, and 5,975,893, as well as on the company's website, which is accessible on the World Wide Web (see, e.g., the URL "invisalign.com"). Examples of tooth-mounted attachments suitable for use with orthodontic appliances are also described in patents and patent applications assigned to Align Technology, Inc., including, for example, U.S. Pat. Nos. 6,309,215 and 6,830,450.

Figure 1B:
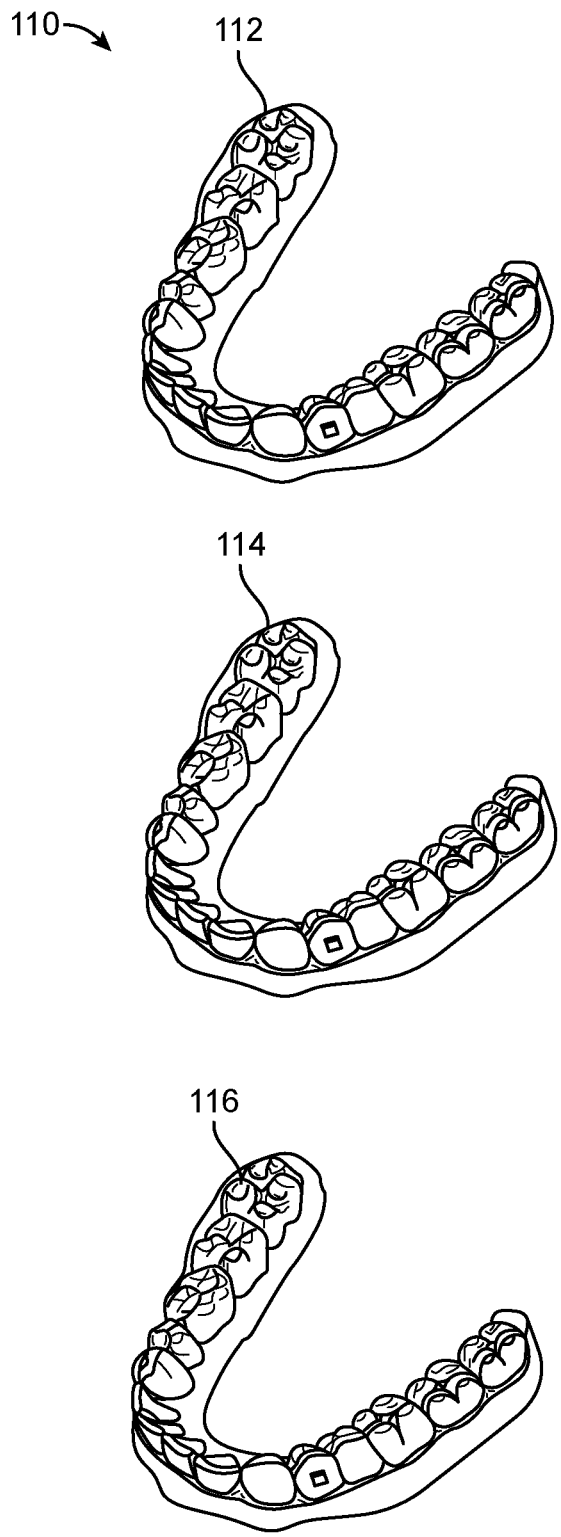
FIG. 1B illustrates a tooth repositioning system, in accordance with embodiments.

FIG. 1B illustrates a tooth repositioning system 110 including a plurality of appliances 112, 114, 116. Any of the appliances described herein can be designed and/or provided as part of a set of a plurality of appliances used in a tooth repositioning system. Each appliance may be configured so a tooth-receiving cavity has a geometry corresponding to an intermediate or final tooth arrangement intended for the appliance. The patient's teeth can be progressively repositioned from an initial tooth arrangement to a target tooth arrangement by placing a series of incremental position adjustment appliances over the patient's teeth. For example, the tooth repositioning system 110 can include a first appliance 112 corresponding to an initial tooth arrangement, one or more intermediate appliances 114 corresponding to one or more intermediate arrangements, and a final appliance 116 corresponding to a target arrangement. A target tooth arrangement can be a planned final tooth arrangement selected for the patient's teeth at the end of all planned orthodontic treatment. Alternatively, a target arrangement can be one of some intermediate arrangements for the patient's teeth during the course of orthodontic treatment, which may include various different treatment scenarios, including, but not limited to, instances where surgery is recommended, where interproximal reduction (IPR) is appropriate, where a progress check is scheduled, where anchor placement is best, where palatal expansion is desirable, where restorative dentistry is involved (e.g., inlays, onlays, crowns, bridges, implants, veneers, and the like), etc. As such, it is understood that a target tooth arrangement can be any planned resulting arrangement for the patient's teeth that follows one or more incremental repositioning stages. Likewise, an initial tooth arrangement can be any initial arrangement for the patient's teeth that is followed by one or more incremental repositioning stages.

Figure 1C:
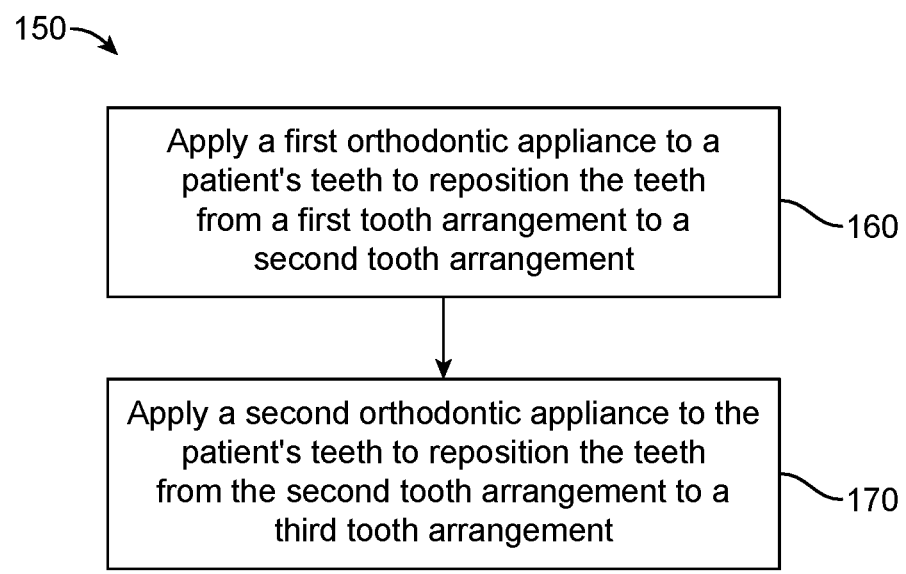
FIG. 1C illustrates a method of orthodontic treatment using a plurality of appliances, in accordance with embodiments.

FIG. 1C illustrates a method 150 of orthodontic treatment using a plurality of appliances, in accordance with embodiments. The method 150 can be practiced using any of the appliances or appliance sets described herein. In step 160, a first orthodontic appliance is applied to a patient's teeth in order to reposition the teeth from a first tooth arrangement to a second tooth arrangement. In step 170, a second orthodontic appliance is applied to the patient's teeth in order to reposition the teeth from the second tooth arrangement to a third tooth arrangement. The method 150 can be repeated as necessary using any suitable number and combination of sequential appliances in order to incrementally reposition the patient's teeth from an initial arrangement to a target arrangement. The appliances can be generated all at the same stage or in sets or batches (e.g., at the beginning of a stage of the treatment), or the appliances can be fabricated one at a time, and the patient can wear each appliance until the pressure of each appliance on the teeth can no longer be felt or until the maximum amount of expressed tooth movement for that given stage has been achieved. A plurality of different appliances (e.g., a set) can be designed and even fabricated prior to the patient wearing any appliance of the plurality. After wearing an appliance for an appropriate period of time, the patient can replace the current appliance with the next appliance in the series until no more appliances remain. The appliances are generally not affixed to the teeth and the patient may place and replace the appliances at any time during the procedure (e.g., patient-removable appliances). The final appliance or several appliances in the series may have a geometry or geometries selected to overcorrect the tooth arrangement. For instance, one or more appliances may have a geometry that would (if fully achieved) move individual teeth beyond the tooth arrangement that has been selected as the "final." Such over-correction may be desirable in order to offset potential relapse after the repositioning method has been terminated (e.g., permit movement of individual teeth back toward their pre-corrected positions). Over-correction may also be beneficial to speed the rate of correction (e.g., an appliance with a geometry that is positioned beyond a desired intermediate or final position may shift the individual teeth toward the position at a greater rate). In such cases, the use of an appliance can be terminated before the teeth reach the positions defined by the appliance. Furthermore, over-correction may be deliberately applied in order to compensate for any inaccuracies or limitations of the appliance.

The various embodiments of the orthodontic appliances presented herein can be fabricated in a wide variety of ways. In some embodiments, the orthodontic appliances herein (or portions thereof) can be produced using direct fabrication, such as additive manufacturing techniques (also referred to herein as "3D printing") or subtractive manufacturing techniques (e.g., milling). In some embodiments, direct fabrication involves forming an object (e.g., an orthodontic appliance or a portion thereof) without using a physical template (e.g., mold, mask etc.) to define the object geometry. Additive manufacturing techniques can be categorized as follows: (1) vat photopolymerization (e.g., stereolithography), in which an object is constructed layer by layer from a vat of liquid photopolymer resin; (2) material jetting, in which material is jetted onto a build platform using either a continuous or drop on demand (DOD) approach; (3) binder jetting, in which alternating layers of a build material (e.g., a powder-based material) and a binding material (e.g., a liquid binder) are deposited by a print head; (4) fused deposition modeling (FDM), in which material is drawn though a nozzle, heated, and deposited layer by layer; (5) powder bed fusion, including but not limited to direct metal laser sintering (DMLS), electron beam melting (EBM), selective heat sintering (SHS), selective laser melting (SLM), and selective laser sintering (SLS); (6) sheet lamination, including but not limited to laminated object manufacturing (LOM) and ultrasonic additive manufacturing (UAM); and (7) directed energy deposition, including but not limited to laser engineering net shaping, directed light fabrication, direct metal deposition, and 3D laser cladding. For example, stereolithography can be used to directly fabricate one or more of the appliances herein. In some embodiments, stereolithography involves selective polymerization of a photosensitive resin (e.g., a photopolymer) according to a desired cross-sectional shape using light (e.g., ultraviolet light). The object geometry can be built up in a layer-by-layer fashion by sequentially polymerizing a plurality of object cross-sections. As another example, the appliances herein can be directly fabricated using selective laser sintering. In some embodiments, selective laser sintering involves using a laser beam to selectively melt and fuse a layer of powdered material according to a desired cross-sectional shape in order to build up the object geometry. As yet another example, the appliances herein can be directly fabricated by fused deposition modeling. In some embodiments, fused deposition modeling involves melting and selectively depositing a thin filament of thermoplastic polymer in a layer-by-layer manner in order to form an object. In yet another example, material jetting can be used to directly fabricate the appliances herein. In some embodiments, material jetting involves jetting or extruding one or more materials onto a build surface in order to form successive layers of the object geometry.

Alternatively or in combination, some embodiments of the appliances herein (or portions thereof) can be produced using indirect fabrication techniques, such as by thermoforming over a positive or negative mold. Indirect fabrication of an orthodontic appliance can involve producing a positive or negative mold of the patient's dentition in a target arrangement (e.g., by rapid prototyping, milling, etc.) and thermoforming one or more sheets of material over the mold in order to generate an appliance shell.

In some embodiments, the direct fabrication methods provided herein build up the object geometry in a layer-by-layer fashion, with successive layers being formed in discrete build steps. Alternatively, or in combination, direct fabrication methods that allow for continuous build-up of an object geometry can be used, referred to herein as "continuous direct fabrication." Various types of continuous direct fabrication methods can be used. As an example, in some embodiments, the appliances herein are fabricated using "continuous liquid interphase printing," in which an object is continuously built up from a reservoir of photopolymerizable resin by forming a gradient of partially cured resin between the building surface of the object and a polymerization-inhibited "dead zone." In some embodiments, a semi-permeable membrane is used to control transport of a photopolymerization inhibitor (e.g., oxygen) into the dead zone in order to form the polymerization gradient. Continuous liquid interphase printing can achieve fabrication speeds about 25 times to about 100 times faster than other direct fabrication methods, and speeds about 1000 times faster can be achieved with the incorporation of cooling systems. Continuous liquid interphase printing is described in U.S. Patent Publication Nos. 2015/0097315, 2015/0097316, and 2015/0102532, the disclosures of each of which are incorporated herein by reference in their entirety.

As another example, a continuous direct fabrication method can achieve continuous build-up of an object geometry by continuous movement of the build platform (e.g., along the vertical or Z-direction) during the irradiation phase, such that the hardening depth of the irradiated photopolymer is controlled by the movement speed. Accordingly, continuous polymerization of material on the build surface can be achieved. Such methods are described in U.S. Pat. No. 7,892,474, the disclosure of which is incorporated herein by reference in its entirety.

In another example, a continuous direct fabrication method can involve extruding a composite material composed of a curable liquid material surrounding a solid strand. The composite material can be extruded along a continuous three-dimensional path in order to form the object. Such methods are described in U.S. Patent Publication No. 2014/0061974, the disclosure of which is incorporated herein by reference in its entirety.

In yet another example, a continuous direct fabrication method utilizes a "heliolithography" approach in which the liquid photopolymer is cured with focused radiation while the build platform is continuously rotated and raised. Accordingly, the object geometry can be continuously built up along a spiral build path. Such methods are described in U.S. Patent Publication No. 2014/0265034, the disclosure of which is incorporated herein by reference in its entirety.

Machine parameters can include curing parameters. For digital light processing (DLP)-based curing systems, curing parameters can include power, curing time, and/or grayscale of the full image. For laser-based curing systems, curing parameters can include power, speed, beam size, beam shape and/or power distribution of the beam. For printing systems, curing parameters can include material drop size, viscosity, and/or curing power. These machine parameters can be monitored and adjusted on a regular basis (e.g., some parameters at every 1-x layers and some parameters after each build) as part of the process control on the fabrication machine. Process control can be achieved by including a sensor on the machine that measures power and other beam parameters every layer or every few seconds and automatically adjusts them with a feedback loop. For DLP machines, gray scale can be measured and calibrated before, during, and/or at the end of each build, and/or at predetermined time intervals (e.g., every $n^{th}$ build, once per hour, once per day, once per week, etc.), depending on the stability of the system. In addition, material properties and/or photo-characteristics can be provided to the fabrication machine, and a machine process control module can use these parameters to adjust machine parameters (e.g., power, time, gray scale, etc.) to compensate for variability in material properties. By implementing process controls for the fabrication machine, reduced variability in appliance accuracy and residual stress can be achieved.

Optionally, the direct fabrication methods described herein allow for fabrication of an appliance including multiple materials, referred to herein as "multi-material direct fabrication." In some embodiments, a multi-material direct fabrication method involves concurrently forming an object from multiple materials in a single manufacturing step. For instance, a multi-tip extrusion apparatus can be used to selectively dispense multiple types of materials from distinct material supply sources in order to fabricate an object from a plurality of different materials. Such methods are described in U.S. Pat. No. 6,749,414, the disclosure of which is incorporated herein by reference in its entirety. Alternatively, or in combination, a multi-material direct fabrication method can involve forming an object from multiple materials in a plurality of sequential manufacturing steps. For instance, a first portion of the object can be formed from a first material in accordance with any of the direct fabrication methods herein, then a second portion of the object can be formed from a second material in accordance with methods herein, and so on, until the entirety of the object has been formed.

Direct fabrication can provide various advantages compared to other manufacturing approaches. For instance, in contrast to indirect fabrication, direct fabrication permits production of an orthodontic appliance without utilizing any molds or templates for shaping the appliance, thus reducing the number of manufacturing steps involved and improving the resolution and accuracy of the final appliance geometry. Additionally, direct fabrication permits precise control over the three-dimensional geometry of the appliance, such as the appliance thickness. Complex structures and/or auxiliary components can be formed integrally as a single piece with the appliance shell in a single manufacturing step, rather than being added to the shell in a separate manufacturing step. In some embodiments, direct fabrication is used to produce appliance geometries that would be difficult to create using alternative manufacturing techniques, such as appliances with very small or fine features, complex geometric shapes, undercuts, interproximal structures, shells with variable thicknesses, and/or internal structures (e.g., for improving strength with reduced weight and material usage). For example, in some embodiments, the direct fabrication approaches herein permit fabrication of an orthodontic appliance with feature sizes of less than or equal to about 5 µm, or within a range from about 5 µm to about 50 µm, or within a range from about 20 µm to about 50 µm.

In some embodiments, the direct fabrication techniques described herein can be used to produce appliances with substantially isotropic material properties, e.g., substantially the same or similar strengths along all directions. In some embodiments, the direct fabrication approaches herein permit production of an orthodontic appliance with a strength that varies by no more than about 25%, about 20%, about 15%, about 10%, about 5%, about 1%, or about 0.5% along all directions. In some embodiments, the direct fabrication techniques described herein can be used to produce appliances with substantially anisotropic material properties (e.g., substantially different strengths along all directions). In some embodiments, the direct fabrication techniques described herein produce appliances with a strength that varies by more than about 0.5%, more than about 1%, more than about 5%, more than about 10%, more than about 15%, more than about 20%, or more than about 25% along all directions. Additionally, the direct fabrication approaches herein can be used to produce orthodontic appliances at a faster speed compared to other manufacturing techniques. In some embodiments, the direct fabrication approaches herein allow for production of an orthodontic appliance in a time interval less than or equal to about 1 hour, about 30 minutes, about 25 minutes, about 20 minutes, about 15 minutes, about 10 minutes, about 5 minutes, about 4 minutes, about 3 minutes, about 2 minutes, about 1 minutes, or about 30 seconds. Such manufacturing speeds allow for rapid "chairside" production of customized appliances, e.g., during a routine appointment or checkup.

In some embodiments, the direct fabrication methods described herein implement process controls for various machine parameters of a direct fabrication system or device in order to ensure that the resultant appliances are fabricated with a high degree of precision. Such precision can be beneficial for ensuring accurate delivery of a desired force system to the teeth in order to effectively elicit tooth movements. Process controls can be implemented to account for process variability arising from multiple sources, such as the material properties, machine parameters, environmental variables, and/or post-processing parameters.

Material properties may vary depending on the properties of raw materials, purity of raw materials, and/or process variables during mixing of the raw materials. In many embodiments, resins or other materials for direct fabrication should be manufactured with tight process control to ensure little variability in photo-characteristics, material properties (e.g., viscosity, surface tension), physical properties (e.g., modulus, strength, elongation) and/or thermal properties (e.g., glass transition temperature, heat deflection temperature). Process control for a material manufacturing process can be achieved with screening of raw materials for physical properties and/or control of temperature, humidity, and/or other process parameters during the mixing process. By implementing process controls for the material manufacturing procedure, reduced variability of process parameters and more uniform material properties for each batch of material can be achieved. Residual variability in material properties can be compensated with process control on the machine, as discussed further herein.

Machine parameters can include curing parameters. For digital light processing (DLP)-based curing systems, curing parameters can include power, curing time, and/or grayscale of the full image. For laser-based curing systems, curing parameters can include power, speed, beam size, beam shape and/or power distribution of the beam. For printing systems, curing parameters can include material drop size, viscosity, and/or curing power. These machine parameters can be monitored and adjusted on a regular basis (e.g., some parameters at every 1-x layers and some parameters after each build) as part of the process control on the fabrication machine. Process control can be achieved by including a sensor on the machine that measures power and other beam parameters every layer or every few seconds and automatically adjusts them with a feedback loop. For DLP machines, gray scale can be measured and calibrated at the end of each build. In addition, material properties and/or photo-characteristics can be provided to the fabrication machine, and a machine process control module can use these parameters to adjust machine parameters (e.g., power, time, gray scale, etc.) to compensate for variability in material properties. By implementing process controls for the fabrication machine, reduced variability in appliance accuracy and residual stress can be achieved.

In many embodiments, environmental variables (e.g., temperature, humidity, Sunlight or exposure to other energy/curing source) are maintained in a tight range to reduce variable in appliance thickness and/or other properties. Optionally, machine parameters can be adjusted to compensate for environmental variables.

In many embodiments, post-processing of appliances includes cleaning, post-curing, and/or support removal processes. Relevant post-processing parameters can include purity of cleaning agent, cleaning pressure and/or temperature, cleaning time, post-curing energy and/or time, and/or consistency of support removal process. These parameters can be measured and adjusted as part of a process control scheme. In addition, appliance physical properties can be varied by modifying the post-processing parameters. Adjusting post-processing machine parameters can provide another way to compensate for variability in material properties and/or machine properties.

The configuration of the orthodontic appliances herein can be determined according to a treatment plan for a patient, e.g., a treatment plan involving successive administration of a plurality of appliances for incrementally repositioning teeth. Computer-based treatment planning and/or appliance manufacturing methods can be used in order to facilitate the design and fabrication of appliances. For instance, one or more of the appliance components described herein can be digitally designed and fabricated with the aid of computer-controlled manufacturing devices (e.g., computer numerical control (CNC) milling, computer-controlled rapid prototyping such as 3D printing, etc.). The computer-based methods presented herein can improve the accuracy, flexibility, and convenience of appliance fabrication.

Figure 2:
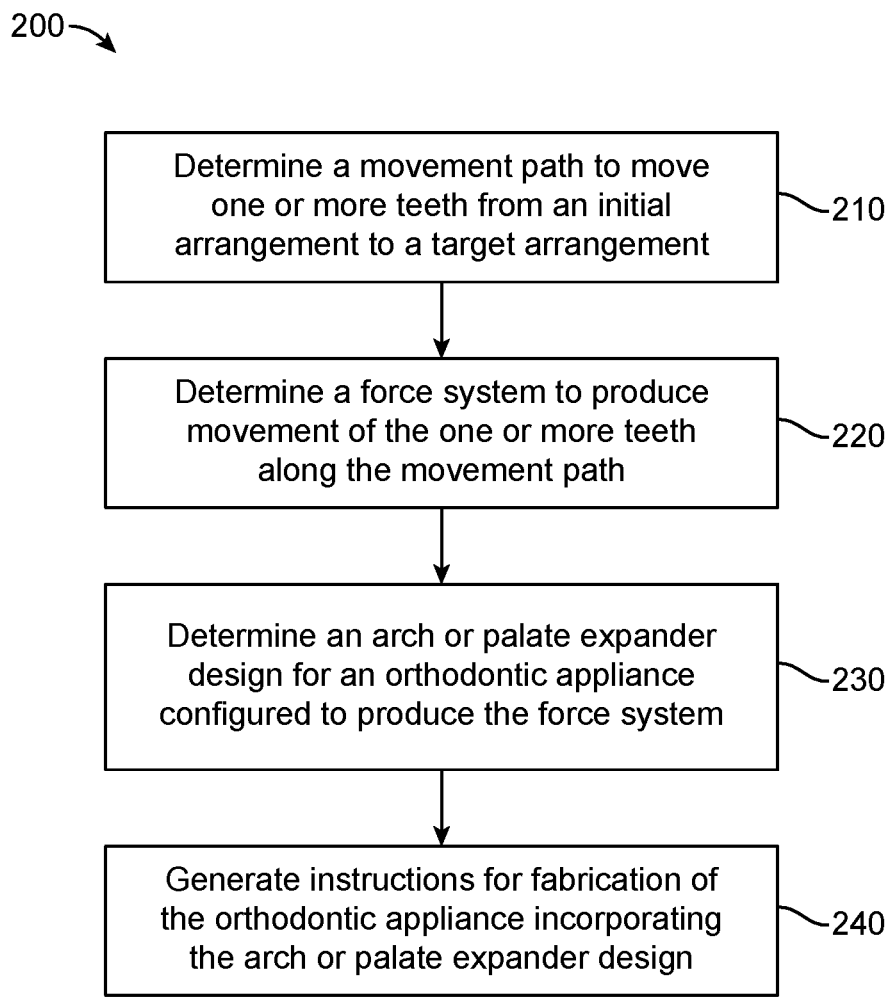
FIG. 2 illustrates a method for designing an orthodontic appliance, in accordance with embodiments.

FIG. 2 illustrates a method 200 for designing an orthodontic appliance to be produced by direct fabrication, in accordance with embodiments. The method 200 can be applied to any embodiment of the orthodontic appliances described herein. Some or all of the steps of the method 200 can be performed by any suitable data processing system or device, e.g., one or more processors configured with suitable instructions.

In step 210, a movement path to move one or more teeth from an initial arrangement to a target arrangement is determined. The initial arrangement can be determined from a mold or a scan of the patient's teeth or mouth tissue, e.g., using wax bites, direct contact scanning, x-ray imaging, tomographic imaging, sonographic imaging, and other techniques for obtaining information about the position and structure of the teeth, jaws, gums and other orthodontically relevant tissue. From the obtained data, a digital data set can be derived that represents the initial (e.g., pretreatment) arrangement of the patient's teeth and other tissues. Optionally, the initial digital data set is processed to segment the tissue constituents from each other. For example, data structures that digitally represent individual tooth crowns can be produced. Advantageously, digital models of entire teeth can be produced, including measured or extrapolated hidden surfaces and root structures, as well as surrounding bone and soft tissue.

The target arrangement of the teeth (e.g., a desired and intended end result of orthodontic treatment) can be received from a clinician in the form of a prescription, can be calculated from basic orthodontic principles, and/or can be extrapolated computationally from a clinical prescription. With a specification of the desired final positions of the teeth and a digital representation of the teeth themselves, the final position and surface geometry of each tooth can be specified to form a complete model of the tooth arrangement at the desired end of treatment.

Having both an initial position and a target position for each tooth, a movement path can be defined for the motion of each tooth. In some embodiments, the movement paths are configured to move the teeth in the quickest fashion with the least amount of round-tripping to bring the teeth from their initial positions to their desired target positions. The tooth paths can optionally be segmented, and the segments can be calculated so that each tooth's motion within a segment stays within threshold limits of linear and rotational translation. In this way, the end points of each path segment can constitute a clinically viable repositioning, and the aggregate of segment end points can constitute a clinically viable sequence of tooth positions, so that moving from one point to the next in the sequence does not result in a collision of teeth.

In step 220, a force system to produce movement of the one or more teeth along the movement path is determined. A force system can include one or more forces and/or one or more torques. Different force systems can result in different types of tooth movement, such as tipping, translation, rotation, extrusion, intrusion, root movement, etc. Biomechanical principles, modeling techniques, force calculation/measurement techniques, and the like, including knowledge and approaches commonly used in orthodontia, may be used to determine the appropriate force system to be applied to the tooth to accomplish the tooth movement. In determining the force system to be applied, sources may be considered including literature, force systems determined by experimentation or virtual modeling, computer-based modeling, clinical experience, minimization of unwanted forces, etc.

The determination of the force system can include constraints on the allowable forces, such as allowable directions and magnitudes, as well as desired motions to be brought about by the applied forces. For example, in fabricating palatal expanders, different movement strategies may be desired for different patients. For example, the amount of force needed to separate the palate can depend on the age of the patient, as very young patients may not have a fully-formed suture. Thus, in juvenile patients and others without fully-closed palatal sutures, palatal expansion can be accomplished with lower force magnitudes. Slower palatal movement can also aid in growing bone to fill the expanding suture. For other patients, a more rapid expansion may be desired, which can be achieved by applying larger forces. These requirements can be incorporated as needed to choose the structure and materials of appliances; for example, by choosing palatal expanders capable of applying large forces for rupturing the palatal suture and/or causing rapid expansion of the palate. Subsequent appliance stages can be designed to apply different amounts of force, such as first applying a large force to break the suture, and then applying smaller forces to keep the suture separated or gradually expand the palate and/or arch.

The determination of the force system can also include modeling of the facial structure of the patient, such as the skeletal structure of the jaw and palate. Scan data of the palate and arch, such as X-ray data or 3D optical scanning data, for example, can be used to determine parameters of the skeletal and muscular system of the patient's mouth, so as to determine forces sufficient to provide a desired expansion of the palate and/or arch. In some embodiments, the thickness and/or density of the mid-palatal suture may be measured, or input by a treating professional. In other embodiments, the treating professional can select an appropriate treatment based on physiological characteristics of the patient. For example, the properties of the palate may also be estimated based on factors such as the patient's age—for example, young juvenile patients will typically require lower forces to expand the suture than older patients, as the suture has not yet fully formed.

In step 230, an arch or palate expander design for an orthodontic appliance configured to produce the force system is determined. Determination of the arch or palate expander design, appliance geometry, material composition, and/or properties can be performed using a treatment or force application simulation environment. A simulation environment can include, e.g., computer modeling systems, biomechanical systems or apparatus, and the like. Optionally, digital models of the appliance and/or teeth can be produced, such as finite element models. The finite element models can be created using computer program application software available from a variety of vendors. For creating solid geometry models, computer aided engineering (CAE) or computer aided design (CAD) programs can be used, such as the AutoCAD® software products available from Autodesk, Inc., of San Rafael, Calif. For creating finite element models and analyzing them, program products from a number of vendors can be used, including finite element analysis packages from ANSYS, Inc., of Canonsburg, Pa., and SIM-ULIA (Abaqus) software products from Dassault Systèmes of Waltham, Mass.

Optionally, one or more arch or palate expander designs can be selected for testing or force modeling. As noted above, a desired tooth movement, as well as a force system required or desired for eliciting the desired tooth movement, can be identified. Using the simulation environment, a candidate arch or palate expander design can be analyzed or modeled for determination of an actual force system resulting from use of the candidate appliance. One or more modifications can optionally be made to a candidate appliance, and force modeling can be further analyzed as described, e.g., in order to iteratively determine an appliance design that produces the desired force system.

In step 240, instructions for fabrication of the orthodontic appliance incorporating the arch or palate expander design are generated. The instructions can be configured to control a fabrication system or device in order to produce the orthodontic appliance with the specified arch or palate expander design. In some embodiments, the instructions are configured for manufacturing the orthodontic appliance using direct fabrication (e.g., stereolithography, selective laser sintering, fused deposition modeling, 3D printing, continuous direct fabrication, multi-material direct fabrication, etc.), in accordance with the various methods presented herein. In alternative embodiments, the instructions can be configured for indirect fabrication of the appliance, e.g., by thermoforming.

Method 200 may comprise additional steps: 1) The upper arch and palate of the patient is scanned intraorally to generate three dimensional data of the palate and upper arch; 2) The three dimensional shape profile of the appliance is determined to provide a gap and teeth engagement structures as described herein.

Although the above steps show a method 200 of designing an orthodontic appliance in accordance with some embodiments, a person of ordinary skill in the art will recognize some variations based on the teaching described herein. Some of the steps may comprise sub-steps. Some of the steps may be repeated as often as desired. One or more steps of the method 200 may be performed with any suitable fabrication system or device, such as the embodiments described herein. Some of the steps may be optional, and the order of the steps can be varied as desired.

Figure 3:
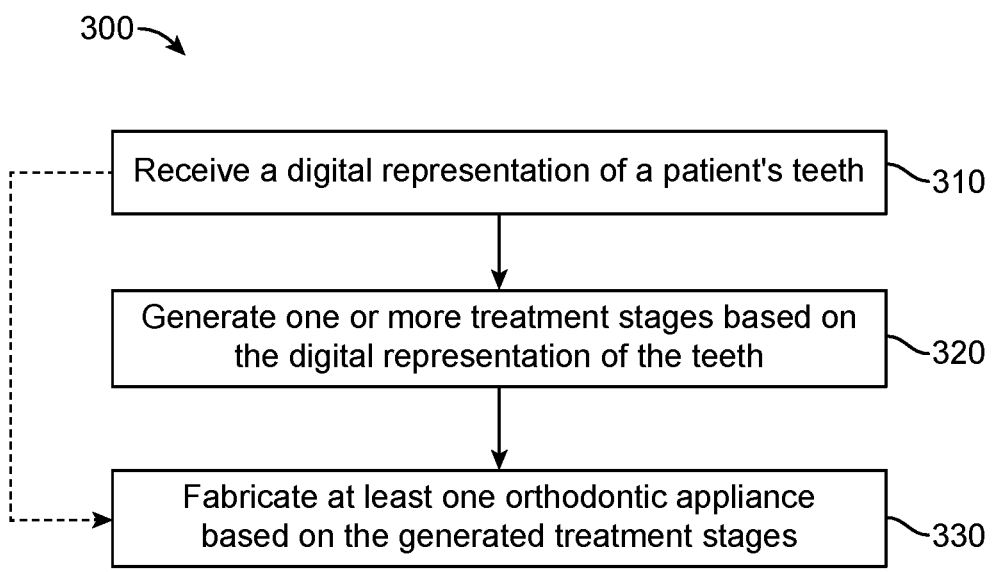
FIG. 3 illustrates a method for digitally planning an orthodontic treatment, in accordance with embodiments.

FIG. 3 illustrates a method 300 for digitally planning an orthodontic treatment and/or design or fabrication of an appliance, in accordance with embodiments. The method 300 can be applied to any of the treatment procedures described herein and can be performed by any suitable data processing system.

In step 310, a digital representation of a patient's teeth is received. The digital representation can include surface topography data for the patient's intraoral cavity (including teeth, gingival tissues, etc.). The surface topography data can be generated by directly scanning the intraoral cavity, a physical model (positive or negative) of the intraoral cavity, or an impression of the intraoral cavity, using a suitable scanning device (e.g., a handheld scanner, desktop scanner, etc.).

In step 320, one or more treatment stages are generated based on the digital representation of the teeth. The treatment stages can be incremental repositioning stages of an orthodontic treatment procedure designed to move one or more of the patient's teeth from an initial tooth arrangement to a target arrangement. For example, the treatment stages can be generated by determining the initial tooth arrangement indicated by the digital representation, determining a target tooth arrangement, and determining movement paths of one or more teeth in the initial arrangement necessary to achieve the target tooth arrangement. The movement path can be optimized based on minimizing the total distance moved, preventing collisions between teeth, avoiding tooth movements that are more difficult to achieve, or any other suitable criteria.

In step 330, at least one orthodontic appliance is fabricated based on the generated treatment stages. For example, a set of appliances can be fabricated, each shaped according a tooth arrangement specified by one of the treatment stages, such that the appliances can be sequentially worn by the patient to incrementally reposition the teeth from the initial arrangement to the target arrangement. The appliance set may include one or more of the orthodontic appliances described herein. The fabrication of the appliance may involve creating a digital model of the appliance to be used as input to a computer-controlled fabrication system. The appliance can be formed using direct fabrication methods, indirect fabrication methods, or combinations thereof, as desired.

In some instances, staging of various arrangements or treatment stages may not be necessary for design and/or fabrication of an appliance. As illustrated by the dashed line in FIG. 3, design and/or fabrication of an orthodontic appliance, and perhaps a particular orthodontic treatment, may include use of a representation of the patient's teeth (e.g., receive a digital representation of the patient's teeth 310), followed by design and/or fabrication of an orthodontic appliance based on a representation of the patient's teeth in the arrangement represented by the received representation.

On-Track Treatment

Figure 4:
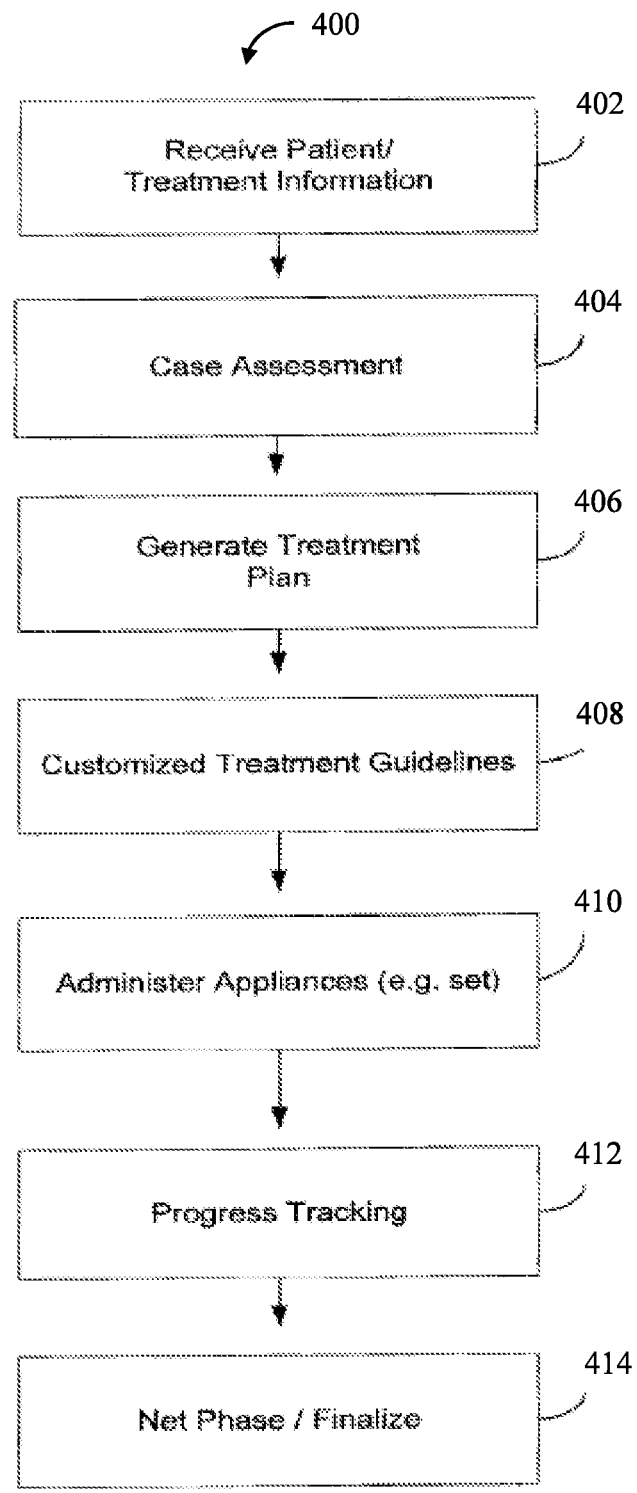
FIG. 4 shows generating and administering treatment according to an embodiment of the present invention.

Referring to FIG. 4, a process 400 according to the present invention is illustrated. Individual aspects of the process are discussed in further detail below. The process includes receiving information regarding the orthodontic condition of the patient and/or treatment information (402), generating an assessment of the case (404), and generating a treatment plan for repositioning a patient's teeth (406). Briefly, a patient/treatment information will include obtaining data comprising an initial arrangement of the patient's teeth, which typically includes obtaining an impression or scan of the patient's teeth prior to the onset of treatment and can further include identification of one or more treatment goals selected by the practitioner and/or patient. A case assessment can be generated (404) so as to assess the complexity or difficulty of moving the particular patient's teeth in general or specifically corresponding to identified treatment goals and may further include practitioner experience and/or comfort level in administering the desired orthodontic treatment. In some cases, however, the assessment can include simply identifying particular treatment options (e.g., appointment planning, progress tracking, etc.) that are of interest to the patient and/or practitioner. The information and/or corresponding treatment plan will include identifying a final or target arrangement of the patient's teeth that is desired, as well as a plurality of planned successive or intermediary tooth arrangements for moving the teeth along a treatment path from the initial arrangement toward the selected final or target arrangement.

The process further includes generating customized treatment guidelines (408). The treatment plan typically includes multiple phases of treatment, with a customized set of treatment guidelines generated that correspond to a phase of the treatment plan. The guidelines will include detailed information on timing and/or content (e.g., specific tasks) to be completed during a given phase of treatment and will be of sufficient detail to guide a practitioner, including a less experienced practitioner or practitioner relatively new to the particular orthodontic treatment process, through the phase of treatment. Since the guidelines are designed to specifically correspond to the treatment plan and provide guidelines on activities specifically identified in the treatment information and/or generated treatment plan, the guidelines are said to be customized. The customized treatment guidelines are then provided to the practitioner so as to help instruct the practitioner as how to deliver a given phase of treatment. As set forth above, appliances can be generated based on the planned arrangements and will be provided to the practitioner and ultimately administered to the patient (410). The appliances are typically provided and/or administered in sets or batches of appliances, such as 2, 3, 4, 5, 6, 7, 8, 9, or more appliances, but are not limited to any particular administrative scheme. Appliances can be provided to the practitioner concurrently with a given set of guidelines, or appliances and guidelines can be provided separately.

After the treatment according to the plan begins and following administration of appliances to the patient, treatment progress tracking, e.g., by teeth matching, is done to assess a current and actual arrangement of the patient's teeth compared to a planned arrangement (412). If the patient's teeth are determined to be "on-track" and progressing according to the treatment plan, then treatment progresses as planned and treatment progresses to the next stage of treatment (414). If the patient's teeth have substantially reached the initially planned final arrangement, then treatment progresses to the final stages of treatment (414). Where the patient's teeth are determined to be tracking according to the treatment plan, but have not yet reached the final arrangement, the next set of appliances can be administered to the patient.

The threshold difference values of a planned position of teeth to actual positions selected as indicating that a patient's teeth have progressed on-track are provided below in Table 1. If a patient's teeth have progressed at or within the threshold values, the progress is considered to be on-track. If a patient's teeth have progressed beyond the threshold values, the progress is considered to be off-track.

TABLE 1

| Type Movement | Difference Actual/Planned |
|---|---|
| Rotations | |
| Upper Central Incisors | 9 degrees |
| Upper Lateral Incisors | 11 degrees |
| Lower Incisors | 11 degrees |
| Upper Cuspids | 11 degrees |
| Lower Cuspids | 9.25 degrees |
| Upper Bicuspids | 7.25 degrees |
| Lower First Bicuspid | 7.25 degrees |
| Lower Second Bicuspid | 7.25 degrees |
| Molars | 6 degrees |
| Extrusion | |
| Anterior | 0.75 mm |
| Posterior | 0.75 mm |
| Intrusion | |
| Anterior | 0.75 mm |
| Posterior | 0.75 mm |
| Angulation | |
| Anterior | 5.5 degrees |
| Posterior | 3.7 degrees |
| Inclination | |
| Anterior | 5.5 degrees |
| Posterior | 3.7 degrees |
| Translation | |
| BL Anterior | 0.7 mm |
| BL Posterior Cuspids | 0.9 mm |
| MD Anterior | 0.45 mm |
| MD Cuspids | 0.45 mm |
| MD Posterior | 0.5 mm |

The patient's teeth are determined to be on track by comparison of the teeth in their current positions with teeth in their expected or planned positions, and by confirming the teeth are within the parameter variance disclosed in Table 1. If the patient's teeth are determined to be on track, then treatment can progress according to the existing or original treatment plan. For example, a patient determined to be progressing on track can be administered one or more subsequent appliances according to the treatment plan, such as the next set of appliances. Treatment can progress to the final stages and/or can reach a point in the treatment plan where bite matching is repeated for a determination of whether a patient's teeth are progressing as planned or if the teeth are off track.

In some embodiments, as further disclosed herein, this disclosure provides methods of treating a patient using a 3D printed orthodontic appliance. In certain embodiments, the method of repositioning a patient's teeth (or, in some embodiments, a singular tooth) comprises:

generating a treatment plan for the patient, the plan comprising tooth arrangements for moving teeth along a treatment path from an initial arrangement toward a final arrangement;

producing a 3D printed orthodontic appliance comprising less than or equal to 20 wt % hydrogen bonding units or less than or equal to 10 wt % hydrogen bonding units; and moving on-track, with the orthodontic appliance, at least one of the patient's teeth toward an intermediate arrangement or a final tooth arrangement. In preferred embodiments, the method further comprises achieving on-track the movement of the patient's teeth to the intermediate arrangement or final tooth arrangement. In some embodiments, producing the 3D printed orthodontic appliance uses the photo-curable resins disclosed further herein. On-track performance can be determined, e.g., from Table 1, above.

In some embodiments, the method further comprises tracking the progression of the patient's teeth along the treatment path after administration of the orthodontic appliance. In certain embodiments, the tracking comprises comparing a current arrangement of the patient's teeth to a planned arrangement of the teeth. As a non-limiting example, following the initial administration of the orthodontic appliance, a period of time passes (e.g., two weeks), a comparison of the now-current arrangement of the patient's teeth (i.e., at two weeks of treatment) can be compared with the teeth arrangement of the treatment plan. In some embodiments, the progression can also be tracked by comparing the current arrangement of the patient's teeth with the initial configuration of the patient's teeth. The period of time can be, for example, greater than 3 days, greater than 4 days, greater than 5 days, greater than 6 days, greater than 7 days, greater than 8 days, greater than 9 days, greater than 10 days, greater than 11 days, greater than 12 days, greater than 13 days, greater than 2 weeks, greater than 3 weeks, greater than 4 weeks, or greater than 2 months. In some embodiments, the period of time can be from at least 3 days to at most 4 weeks, from at least 3 days to at most 3 weeks, from at least 3 days to at most 2 weeks, from at least 4 days to at most 4 weeks, from at least 4 days to at most 3 weeks, or from at least 4 days to at most 2 weeks. In certain embodiments, the period of time can restart following the administration of a new orthodontic appliance.

In some embodiments, greater than 50%, greater than 55%, greater than 60%, greater than 65%, greater than 70%, greater than 75%, greater than 80%, greater than 85%, greater than 90%, greater than 91%, greater than 92%, greater than 93%, greater than 94%, greater than 95%, greater than 96%, greater than 97%, greater than 98%, or greater than 99% of the patient's teeth are on track with the treatment plan after a period of time of using an orthodontic appliance as disclosed further herein. In some embodiments, the period of time is 3 days, 4 days, 5 days, 6 days, 7 days, 8 days, 9 days, 10 days, 11 days, 12 days, 13 days, 2 weeks, 3 weeks, 4 weeks, or greater than 4 weeks.

Properties After Use

In some embodiments of the method disclosed above, the 3D printed orthodontic appliance has a retained repositioning force (i.e., the repositioning force after the orthodontic appliance has been applied to or worn by the patient over a period of time), and the retained repositioning force to at least one of the patient's teeth after the period of time is at least 10%, at least 20%, at least 30%, at least 40%, at least 50%, at least 55%, at least 60%, at least 65%, at least 70%, at least 75%, at least 80%, at least 85%, at least 90%, at least 95%, at least 96%, at least 97%, at least 98%, or at least 99% of the repositioning force initially provided to the at least one of the patient's teeth (i.e., with initial application of the orthodontic appliance). In some embodiments, the period of time is 3 days, 4 days, 5 days, 6 days, 7 days, 8 days, 9 days, 10 days, 11 days, 12 days, 13 days, 2 weeks, 3 weeks, 4 weeks, or greater than 4 weeks.

In preferred embodiments, the orthodontic appliances disclosed herein can provide on-track movement of at least one of the patient's teeth. On-track movement has been described further herein, e.g., at Table 1. In some embodiments, the orthodontic appliances disclosed herein can be used to achieve on-track movement of at least one of the patient's teeth to an intermediate tooth arrangement. In some embodiments, the orthodontic appliances disclosed herein can be used to achieve on-track movement of at least one of the patient's teeth to a final tooth arrangement.

In some embodiments, prior to moving on-track, with the orthodontic appliance, at least one of the patient's teeth toward the intermediate arrangement or the final tooth arrangement, the orthodontic appliance comprises a first flexural stress; and after achieving on-track the movement of the at least one of the patient's teeth to the intermediate arrangement or the final tooth arrangement, the orthodontic appliance comprises a second flexural stress.

As provided herein, the methods disclosed can use the orthodontic appliances further disclosed herein. Said orthodontic appliances can be directly fabricated using, e.g., the resins disclosed herein. In certain embodiments, the direct fabrication comprises cross-linking the resin.

The appliances formed from the resins disclosed herein provide improved durability, strength, and flexibility, which in turn improve the rate of on-track progression in treatment plans. In some embodiments, greater than 60%, greater than 70%, greater than 80%, greater than 90%, or greater than 95% of patients treated with the orthodontic appliances disclosed herein (e.g., an aligner) are classified as on-track in a given treatment stage. In certain embodiments, greater than 60%, greater than 70%, greater than 80%, greater than 90%, or greater than 95% of patients treated with the orthodontic appliances disclosed herein (e.g., an aligner) have greater than 50%, greater than 55%, greater than 60%, greater than 65%, greater than 70%, greater than 75%, greater than 80%, greater than 85%, greater than 90%, or greater than 95% of their tooth movements classified as on-track.

EXAMPLES

The specific compositions, synthesis, formulations, and descriptions of any of the materials, devices, systems, and components thereof, of the present disclosure can be readily varied depending upon the intended application, as will be apparent to those of skill in the art in view of the disclosure herein. Moreover, it is understood that the examples and aspects described herein are for illustrative purposes only and that various modifications or changes in light thereof can be suggested to persons skilled in the art and are included within the spirit and purview of this application and scope of the appended claims. Numerous different combinations of aspects described herein are possible, and such combinations are considered part of the present disclosure. In addition, all features discussed in connection with any one aspect herein can be readily adapted for use in other aspects herein. The use of different terms or reference numerals for similar features in different aspects does not necessarily imply differences other than those expressly set forth. Accordingly, the present disclosure is intended to be described solely by reference to the appended claims, and not limited to the aspects disclosed herein.

Example 1

Formation of Polymeric Materials from Photo-Curable Resins

This example describes the generation of photo-curable resins, and the formation of polymeric materials from said photo-curable resins. Also described are exemplary materials properties from the polymeric materials.

Photo-curable resins 1-14 were generated by combining 70 wt % of the oligomer and 30 wt % of the reactive diluent, as shown in Table 2:

TABLE 2

| Photo-curable Resin | Oligomer | Reactive Diluent |
| --- | --- | --- |
| 1 | TNM2 | HSMA |
| 2 | TNM2 with TEGDMA | HSMA |
| 3 | BRC-4421 | IBOA |
| 4 | BRC-4421 | HSMA |
| 5 | BRC-4421 | — |
| 6 | BR-742S | IBOA |
| 7 | BRC-843D | IBOA |
| 8 | BRC-443 | IBOA |
| 9 | BR-643 | IBOA |
| 10 | BRC-443D | IBOA |
| 11 | BR-640D | IBOA |
| 12 | BRC-841 | IBOA |
| 13 | IH-1000 | IBOA |
| 14 | TEAI-1000 | IBOA |

For photo-curable resin 5, the composition comprised 100 wt % oligomer. To each mixture was added 2 phr (parts per hundred resin) TPO-L as a photoinitiator.

IBOA is isobornyl acrylate; HSMA is 3,3,5-trimethcyclohexyl 2-(methacryloxy)benzoate; TEGDMA is triethylene glycol dimethacrylate; BRC-4421 is a difunctional aliphatic hydrophobic urethane acrylate; BR-742S is a polyester urethane acrylate; BRC-843D is a hydrophobic urethane acrylate; BRC-443 is a hydrophobic urethane acrylate; BR-643 is a polybutadiene urethane acrylate; BRC-443D is a hydrophobic urethane acrylate; BR-640D is a polybutadiene urethane acrylate oligomer; BRC-841 is a hydrophobic urethane acrylate; IH-1000 is a urethane acrylic polybutadiene; TEAI-1000 is a polybutadiene acrylate resin with (meth)acryl groups attached to both ends of either polybutadiene or hydrogenated polybutadiene via a urethane bond; and TNM2 has the following chemical formula:

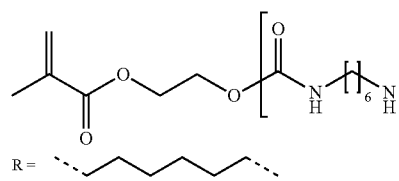
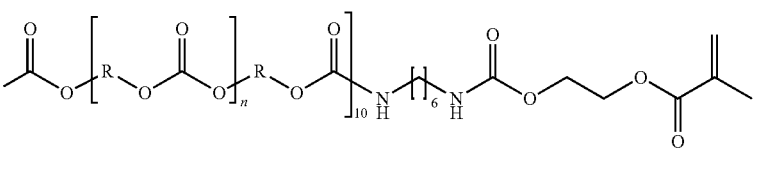

R = 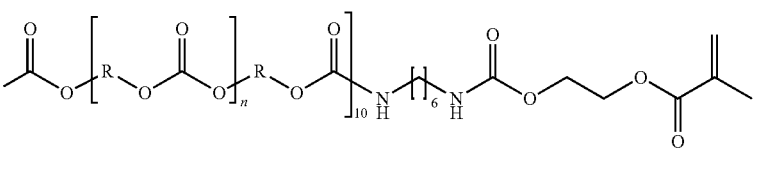

n = 7-8

The prepared resins were weighed into silicone molds having the desired geometry. Each mold was allowed to sit on a flat surface until the resin was evenly distributed in the mold. Each mold was then placed in a Dymax Flood Lamp (Model 2000) and cured for 90 seconds at room temperature. If a thermal initiator is added, a thermal post-treatment on the sample is performed by placing the material in an oven at 90° C. for 3-5 minutes. Photo-curable resins 1-14 were cured to form polymeric materials 1-14, respectively. Prior to measurements of water uptake percentage and stress remaining, samples were placed in jars containing deionized water at 37° C. for 24 hours.

Water uptake percentages of the cured and soaked polymer materials were measured. The mass of samples were measured before and after the soak of samples in deionized water at 37° C. for 24 hours. Percent increase of mass was used to determine water uptake percentage. The results of the water uptake measurements are provided in Table 3, below:

TABLE 3

| Polymeric Material | Water Uptake (%) |
| --- | --- |
| 3 | 0.62 ± 0.15 |
| 4 | 0.74 ± 0.04 |
| 6 | 1.00 ± 0.02 |
| 7 | 0.53 ± 0.02 |
| 8 | 0.54 ± 0.06 |
| 9 | 0.22 ± 0.09 |
| 11 | 0.11 |
| 12 | 1.44 |

Polybutadiene urethane acrylate polymeric materials 9 and 11 had excellent water uptake properties. Urethane acrylate polymeric materials 7 and 8 also showed favorable uptake properties. Polymeric material 6 (polyester urethane acrylate) and polymeric material 12 (hydrophobic urethane acrylate) had relatively high levels of water uptake (1% or greater) and were therefore more likely to have poor measurements for flexural stress remaining.

Tensile modulus of the cured materials were measured using ASTM D1708. The results of the tensile modulus measurements are provided in Table 4, below:

TABLE 4

| Polymeric Material | Tensile Modulus (MPa) |
| --- | --- |
| 2 | 329 |
| 3 | 484 |
| 4 | 556 |
| 5 | 36 |
| 6 | 866 |
| 7 | 105 |
| 8 | 61 |
| 9 | 274 |

TABLE 4-continued

| Polymeric Material | Tensile Modulus (MPa) |
| --- | --- |
| 10 | 146 |
| 12 | 1908 |
| 13 | 9 |
| 14 | 10 |

Polymeric materials having a tensile modulus greater than about 200 MPa were considered to provide sufficient force of interest.

Elongation at break of the cured polymer materials were measured using ASTM D1708. The results of the tensile modulus measurements are provided in Table 5, below:

TABLE 5

| Polymeric Material | Elongation at Break (%) |
| --- | --- |
| 1 | 427 |
| 2 | 106 |
| 3 | 102 |
| 4 | 67 |
| 5 | 116 |
| 6 | 48 |
| 7 | 83 |
| 8 | 104 |
| 9 | 33 |
| 10 | 100 |
| 11 | 114 |
| 12 | 13 |
| 13 | 103 |
| 14 | 96 |

Prior to curing, the viscosity of photo-curable resins was measured using a TA Instruments Discovery HR-2 rheometer, or viscosity values were provided by manufacturer. The viscosity values are provided in Table 6, below:

TABLE 6

| Photo-Curable Resin | Viscosity (cP at 25° C.) |
| --- | --- |
| 1 | Solid |
| 2 | Solid |
| 3 | 6,800 |
| 6 | 16,500 |
| 7 | 5,400 |
| 8 | 14,500 |
| 9 | 18,900 |
| 10 | 16,800 |
| 11 | 14,700 |
| 12 | 27,000 |

Photo-curable resins 1 and 2, comprising TNM2, formed solid materials, and were thus considered too viscous to use for applications of 3D printing. On the other side of the viscosity measurements, resins 3 and 7 (hydrophobic urethane acrylates) showed low viscosity properties and could readily be used in direct fabrication.

Of the resins tested, resin 3 showed a favorable balance of characteristics. Resin 3 had a low viscosity (6,800 cP at 25° C.), a low water uptake of the cured polymeric material (0.62%), and a high tensile modulus of the cured polymeric material (484 MPa).

Example 2

Direct Fabrication of Polymeric Materials from Photo-Curable Resins

This example describes the direct fabrication of polymeric materials from photo-curable resins.

Printed parts were obtained using an Asiga digital light projection (DLP) printer. The photo-curable resins from Example 1 were introduced to the DLP printer, and cured polymeric material was obtained in specified shapes. The photo-curable low-viscosity resins are compatible with use of conventional 3D printers, and the cured polymeric materials have good mechanical properties.

Example 3

Treatment Using an Orthodontic Appliance

This example describes the use of a directly 3D printed orthodontic appliance to move a patient's teeth according to a treatment plan. This example also describes the characteristics that the orthodontic appliance can have following its use, in contrast to its characteristics prior to use.

A patient in need of, or desirous of, a therapeutic treatment to rearrange at least one tooth has their teeth arrangement assessed. An orthodontic treatment plan is generated for the patient. The orthodontic treatment plan comprises a plurality of intermediate tooth arrangements for moving teeth along a treatment path, from the initial arrangement (e.g., that which was initially assessed) toward a final arrangement. The treatment plan includes the use of an orthodontic appliance, fabricated using photo-curable resins and methods disclosed further herein, to provide orthodontic appliances having low levels of hydrogen bonding units. In some embodiments, a plurality of orthodontic appliances are used, each of which can be fabricated using the photo-curable resins and methods disclosed further herein.

The orthodontic appliances are provided, and iteratively applied to the patient's teeth to move the teeth through each of the intermediate tooth arrangements toward the final arrangement. The patient's tooth movement is tracked. A comparison is made between the patient's actual teeth arrangement and the planned intermediate arrangement. Where the patient's teeth are determined to be tracking according to the treatment plan, but have not yet reached the final arrangement, the next set of appliances can be administered to the patient. The threshold difference values of a planned position of teeth to actual positions selected as indicating that a patient's teeth have progressed on-track are provided above in Table 1. If a patient's teeth have progressed at or within the threshold values, the progress is considered to be on-track. Favorably, the use of the appliances disclosed herein increases the probability of on-track tooth movement.

The assessment and determination of whether treatment is on-track can be conducted, for example, 1 week (7 days) following the initial application of an orthodontic appliance. Following this period of application, additional parameters relating to assessing the durability of the orthodontic appliance can also be conducted. For example, relative repositioning force (compared to that which was initially provided by the appliance), remaining flexural stress, relative flexural modulus, and relative elongation at break can be determined.

What is claimed is:

1. An orthodontic appliance comprising a polymeric material formed from a photo-curable resin, the photo-curable resin comprising:
   an oligomer having a number-average molecular weight of greater than 3,000 Da; and
   an initiator,
   wherein the photo-curable resin comprises less than 8 wt % hydrogen bonding units and has a viscosity less than or equal to 15,000 cP at 25° C., and
   wherein the photo-curable resin further comprises one or more of: a crosslinking modifier, a light blocker, a solvent, and a glass transition temperature modifier.

2. The orthodontic appliance of claim 1, wherein the polymeric material comprises a water uptake of less than 25 wt %, less than 20 wt %, less than 15 wt %, less than 10 wt %, less than 5 wt %, less than 4 wt %, less than 3 wt %, less than 2 wt %, less than 1 wt %, less than 0.5 wt %, less than 0.25 wt %, or less than 0.1 wt %.

3. The orthodontic appliance of claim 1, wherein the number-average molecular weight of the oligomer is from 9 kDa to 20 kDa.

4. The orthodontic appliance of claim 1, wherein the oligomer comprises a plurality of monomers, and an average chain length of the oligomer is from 20 to 200 monomers.

5. The orthodontic appliance of claim 1, wherein the photo-curable resin has a viscosity from 30 cP to 50,000 cP at a printing temperature.

6. The orthodontic appliance of claim 5, wherein the printing temperature is from 20° C. to 150° C.

7. The orthodontic appliance of claim 1, wherein the initiator comprises a photoinitiator.

8. The orthodontic appliance of claim 1, wherein the initiator comprises a thermal initiator.

9. The orthodontic appliance of claim 8, wherein the thermal initiator comprises an organic peroxide.

10. The orthodontic appliance of claim 1, further comprising a reactive diluent.

11. The orthodontic appliance of claim 1, wherein the photo-curable resin comprises less than 90% of the solvent by weight.

12. The orthodontic appliance of claim 1, wherein the oligomer comprises an aliphatic urethane (meth)acrylate.

13. The orthodontic appliance of claim 1, wherein the oligomer comprises two or more functional groups.

14. The orthodontic appliance of claim 13, wherein the oligomer is difunctional.

15. The orthodontic appliance of claim 1, wherein the oligomer is monofunctional.

16. The orthodontic appliance of claim 1, wherein the photo-curable resin comprises a plurality of oligomers, and wherein the plurality of oligomers comprise a monofunctional oligomer, a difunctional oligomer, a multifunctional oligomer, or a combination thereof.

17. The orthodontic appliance of claim 1, wherein a polymer formed from the oligomer is hydrophobic.

18. The orthodontic appliance of claim 1, wherein the polymeric material formed from the photo-curable resin is hydrophobic.

19. The orthodontic appliance of claim 1, wherein the photo-curable resin comprises 0.5-99.5 wt % of the oligomer, 1-99 wt % of the oligomer, 10-95 wt % of the oligomer, 20-90 wt % of the oligomer, 25-60 wt % of the oligomer, or wt % of the oligomer.

20. The orthodontic appliance of claim 19, wherein the photo-curable resin comprises 25-60 wt % of the oligomer.

21. The orthodontic appliance of claim 19, wherein the photo-curable resin comprises 99.5 wt % or less of the oligomer.

22. The orthodontic appliance of claim 1, wherein the polymeric material has a tensile modulus greater than or equal to 200 MPa after 24 hours in a wet environment at 37° C.

23. The orthodontic appliance of claim 1, wherein the polymeric material has a flexural stress of greater than or equal to 1.5 MPa remaining after 24 hours in a wet environment at 37° C.

24. The orthodontic appliance of claim 1, wherein the polymeric material has a hardness from 60 Shore A to 85 Shore D after 24 hours in a wet environment at 37° C.

25. The orthodontic appliance of claim 1, wherein the polymeric material has an elongation at break greater than or equal to 15% after 24 hours in a wet environment at 37° C.

26. The orthodontic appliance of claim 1, wherein the polymeric material has greater than 70% of visible light passing through the polymeric material after 24 hours in a wet environment at 37° C.

27. A curable material, comprising:
    an oligomer having a number-average molecular weight of greater than 3,000 Da;
    an initiator; and
    one or more of a crosslinking modifier, a light blocker, a solvent, and a glass transition temperature modifier;
    wherein the curable material comprises less than 8 wt % hydrogen bonding units and has a viscosity less than or equal to 15,000 cP at 25° C., and
    wherein the curable material is incorporated into a polymeric material, wherein the polymeric material forms an orthodontic appliance.

28. The curable material of claim 27, wherein the polymeric material has a hardness from 60 Shore A to 85 Shore D after 24 hours in a wet environment at 37° C.

\* \* \* \* \*